United States Patent
Rehwinkel et al.

(10) Patent No.: US 7,442,794 B2
(45) Date of Patent: Oct. 28, 2008

(54) REARRANGED PENTANOLS, A PROCESS FOR THEIR PRODUCTION AND THEIR USE AS ANTI-INFLAMMATORY AGENTS

(75) Inventors: Hartmut Rehwinkel, Berlin (DE); Stefan Baeurle, Berlin (DE); Markus Berger, Berlin (DE); Norbert Schmees, Berlin (DE); Heike Schaecke, Berlin (DE); Konrad Krolikiewicz, Berlin (DE); Anne Mengel, Berlin (DE); Duy Nguyen, Berlin (DE); Stefan Jaroch, Berlin (DE); Werner Skuballa, Berlin (DE)

(73) Assignee: Schering AG, Berlin (DE)

( * ) Notice: Subject to any disclaimer, the term of this patent is extended or adjusted under 35 U.S.C. 154(b) by 637 days.

(21) Appl. No.: 10/960,757

(22) Filed: Oct. 8, 2004

(65) Prior Publication Data
US 2005/0131226 A1   Jun. 16, 2005

Related U.S. Application Data

(60) Provisional application No. 60/511,576, filed on Oct. 16, 2003.

(30) Foreign Application Priority Data

Oct. 8, 2003 (DE) .............. 103 47 385

(51) Int. Cl.
C07D 237/00  (2006.01)
C07D 239/00  (2006.01)
C07D 453/00  (2006.01)
C07D 217/00  (2006.01)
C07D 231/00  (2006.01)
C07D 209/00  (2006.01)
C07D 311/00  (2006.01)
C07D 407/00  (2006.01)
C07D 493/00  (2006.01)

(52) U.S. Cl. .............. 544/235; 544/253; 546/134; 546/139; 548/356.5; 548/472; 549/232; 564/415

(58) Field of Classification Search .............. None
See application file for complete search history.

(56) References Cited

U.S. PATENT DOCUMENTS

| 6,323,199 | B1 | 11/2001 | Lehmann et al. |
| 2002/0077356 | A1 | 6/2002 | Jaroch et al. |
| 2005/0131226 | A1 | 6/2005 | Rehwinkel et al. |

FOREIGN PATENT DOCUMENTS

| DE | 19856475 A1 | 5/2000 |
| EP | 1375517 | 1/2004 |
| EP | 1670778 B1 | 11/2006 |
| WO | WO 00/32584 | 6/2000 |
| WO | WO 02/10143 | 2/2002 |

OTHER PUBLICATIONS

Uozumi Y et al: "Asymmetric Aza-Claisen Rearrangement of Allyl Imidates Catalyzed by Homochiral Cationic Palladium (II) Complexes" Tetrahedron: Asymmetry, Elsevier Science Publishers, Amsterdam, NL, Bd. 9, Nr. 6, Mar. 27, 1998, seiten 1065-1072.

*Primary Examiner*—Brian J Davis
(74) *Attorney, Agent, or Firm*—Millen, White, Zelano, Branigan, P.C.

(57) ABSTRACT

The invention relates to the compounds of formula I,

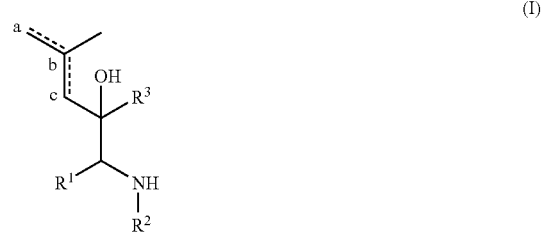

(I)

a process for their production and their use as anti-inflammatory agents.

10 Claims, No Drawings

REARRANGED PENTANOLS, A PROCESS FOR THEIR PRODUCTION AND THEIR USE AS ANTI-INFLAMMATORY AGENTS

This application claims benefit of the filing date of U.S. Provisional Application Ser. No. 60/511,576, filed Oct. 16, 2003.

The invention relates to compounds of formula I, a process for their production and their use as anti-inflammatory agents.

From the prior art of DE 100 38 639 and WO02/10143, anti-inflammatory agents of the following general formula

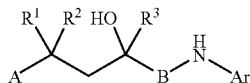

are known, whereby the Ar radical comprises phthalides, thiophthalides, benzoxazinones or phthalazinones. In the experiment, these compounds show dissociations of action between anti-inflammatory and undesirable metabolic actions and are superior to the previously described nonsteroidal glucocorticoids or exhibit at least just as good an action.

The selectivity of the compounds of the prior art compared to the other steroid receptors still requires improvement, however.

It was therefore the object of this invention to make available compounds whose selectivity is improved compared to the other steroid receptors.

This object is achieved by the compounds according to the claims.

This invention therefore relates to compounds of general formula I

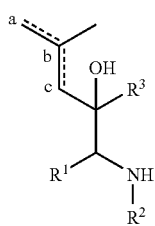

(I)

in which
- $R^1$ means an optionally substituted phenyl radical,
- $R^2$ means a monocyclic, or bicyclic, aromatic, partially aromatic, or non-aromatic ring system, which optionally contains 1-3 nitrogen atoms, 1-2 oxygen atoms and/or 1-2 sulfur atoms and optionally is substituted in one or more places by a radical that is selected from the group carbonyl, halogen, hydroxy, or ($C_1$-$C_5$)-alkyl, which optionally can be substituted by 1-3 hydroxy groups, 1-3 ($C_1$-$C_5$)alkoxy groups and/or 1-3 $COOR^6$ groups, ($C_1$-$C_5$)alkoxy, ($C_1$-$C_5$)-alkylthio, ($C_1$-$C_5$)-perfluoroalkyl, cyano, nitro, or two substituents together form a group that is selected from the groups —O—$(CH_2)_n$—O—, —O—$(CH_2)_n$—$CH_2$—, —O—CH═CH—, —$(CH_2)_{n+2}$—, —NH—$(CH_2)_{n+1}$—, —N($C_1$-$C_3$-alkyl)-$(CH_2)_{n+1}$—, and —NH—N═CH—, whereby n=1 or 2, and the terminal oxygen atoms and/or carbon atoms and/or nitrogen atoms are linked to directly adjacent ring-carbon atoms, $NR^4R^5$, whereby $R^4$ and $R^5$, independently of one another, can be hydrogen, $C_1$-$C_5$-alkyl or (CO)—$C_1$-$C_5$-alkyl, $COOR^6$, whereby $R^6$ means hydrogen or a $C_1$-$C_5$-alkyl group, (CO)$NR^7R^8$, whereby $R^7$ and $R^8$, independently of one another, mean hydrogen or a $C_1$-$C_5$-alkyl group, or a ($C_1$-$C_5$-alkylene)—O—(CO)—($C_1$-$C_5$)alkyl group, $R^3$ means an optionally partially or completely fluorinated $C_1$-$C_3$-alkyl group, and the broken line means a double bond between atoms a and b or a double bond between atoms b and c or only a single bond between atoms a and b, as well as b and c, as well as their racemates or separately present stereoisomers, and optionally their physiologically compatible salts.

Stereoisomers of general formula I, in which
- $R^1$ means an optionally substituted phenyl radical,
- $R^2$ means a monocyclic or bicyclic aromatic, partially aromatic or non-aromatic ring system, which optionally contains 1-3 nitrogen atoms, 1-2 oxygen atoms and/or 1-2 sulfur atoms and optionally is substituted in one or more places by a radical that is selected from the group carbonyl, halogen, hydroxy, ($C_1$-$C_5$)-alkyl, which optionally can be substituted by 1-3 hydroxy groups, 1-3 ($C_1$-$C_5$)alkoxy groups and/or 1-3 $COOR^6$ groups, ($C_1$-$C_5$)alkoxy, ($C_1$-$C_5$)-alkylthio, ($C_1$-$C_5$)-perfluoroalkyl, cyano, nitro, or $NR^4R^5$, whereby $R^4$ and $R^5$, independently of one another, can be hydrogen, $C_1$-$C_5$-alkyl or (CO)—$C_1$-$C_5$-alkyl, $COOR^6$, whereby $R^6$ means hydrogen or a $C_1$-$C_5$-alkyl group, (CO)$NR^7R^8$, whereby $R^7$ and $R^8$, independently of one another, mean hydrogen or a $C_1$-$C_5$-alkyl group, or a ($C_1$-$C_5$-alkylene)-O—(CO)—($C_1$-$C_5$)alkyl group, $R^3$ means a $C_1$-$C_3$-alkyl group or a partially or completely fluorinated $C_1$-$C_3$-alkyl group, and the dotted line means a double bond between atoms a and b or a double bond between atoms b and c or only a single bond between atoms a and b as well as b and c, as well as their racemates or separately present stereoisomers and optionally their physiologically compatible salts, are another subject of the invention.

The compounds of general formula I, in which the phenyl radical $R^1$ is substituted by one or more radicals from the group $C_1$-$C_5$-alkyl, $C_1$-$C_5$alkoxy, $C_1$-$C_5$-alkylthio, $C_1$-$C_5$-perfluoroalkyl, halogen, hydroxy, cyano, nitro, —O—$(CH_2)_n$—O—, —O—$(CH_2)_n$—$CH_2$—, —O—CH═CH—, —$(CH_2)_{n+2}$—, —NH—$(CH_2)_{n+1}$—, N($C_1$-$C_3$-alkyl)-$(CH_2)_{n+1}$, or —NH—N═CH—, whereby n=1 or 2, and the terminal oxygen atoms and/or carbon atoms and/or nitrogen atoms are linked to directly adjacent ring-carbon atoms, or $NR^4R^5$, whereby $R^4$ and $R^5$, independently of one another, can be hydrogen, $C_1$-$C_5$-alkyl or (CO)—$C_1$-$C_5$-alkyl, are another subject of the invention. $C_1$-$C_5$-Alkyl, $C_1$-$C_5$-alkoxy, hydroxy and halogen are preferred.

Preferred subjects of the invention are compounds that as $R^1$ contain a di- or tri-substituted phenyl radical.

Preferred substituents for the group $R^1$ are an alkanoyl group, $C_1$-$C_5$-alkyl, $C_1$-$C_5$-alkoxy, hydroxy, halogen, cyano, —O—$(CH_2)_n$—O—, —O—$(CH_2)_n$—$CH_2$—, —O—CH═CH—, and —$(CH_2)_{n+2}$—; especially preferred substituents for the group $R^1$ are an alkanoyl group, $C_1$-$C_5$-alkyl, $C_1$-$C_5$-alkoxy, hydroxy, halogen and cyano.

With alkanoyl, a radical $(C_1$-$C_5)$alkyl-(CO)— is meant.

Compounds of general formula I, in which $R^2$ means a monocyclic or bicyclic, aromatic or partially aromatic heterocyclic ring system, in particular a bicyclic ring system, are a subject of the invention.

With the definition of a monocyclic or bicyclic aromatic, partially aromatic or non-aromatic ring system, which optionally contains 1-3 nitrogen atoms and/or 1-2 oxygen atoms and/or 1-2 sulfur atoms, aromatic rings systems are bicyclic ring systems that contain only one aromatic ring comprising aliphatic ring systems that can contain 1-7 heteroatoms or else contain no heteroatoms.

Compounds of general formula I, in which $R^2$ means an optionally substituted phthalidyl, isoindolyl, dihydroindolyl, dihydroisoindolyl, dihydroisoquinolinyl, thiophthalidyl, benzoxazinonyl, phthalazinonyl, quinolinyl, isoquinolinyl, quinolonyl, isoquinolonyl, indazolyl, benzothiazolyl, quinazolinyl, quinoxalinyl, cinnolinyl, phthalazinyl, 1,7- or 1,8-naphthyridinyl, dihydroindolonyl, dihydroisoindolonyl, benzimidazole or indolyl group that is linked via any position, especially if these heterocyclic systems are substituted, are a preferred subject of the invention if they are substituted with 0 to 3 of the same or different radicals from the group $C_1$-$C_3$-alkyl, hydroxy, carbonyl or halogen, and are an especially preferred subject of the invention if they are substituted with methyl, chlorine or fluorine.

Compounds of general formula I, in which $R^2$ means a phthalidyl, thiophthalidyl, benzoxazinonyl, phthalazinonyl, quinolinyl, isoquinolinyl, quinolonyl, isoquinolonyl, indazolyl, benzothiazolyl, quinazolinyl, quinoxalinyl, cinnolinyl, phthalazinyl, 1,7- or 1,8-naphthyridinyl, dihydroindolonyl, dihydroisoindolonyl, benzimidazole or indolyl group that is linked via any position, are another subject of the invention.

Compounds of formula I that for $R^2$ carry a coumarinyl or isocoumarinyl radical, in particular the isocoumarinyl radical, which optionally can be substituted with 0 to 3 of the same or different radicals from the group $C_1$-$C_3$-alkyl, hydroxy, carbonyl or halogen, in particular with methyl, chlorine or fluorine, especially the compound of Example 9, are a subject of the invention.

$R^2$ can be substituted in one or more places with a radical from the group carbonyl, halogen, hydroxy, $(C_1$-$C_5)$-alkyl, $(C_1$-$C_5)$alkoxy, $(C_1$-$C_5)$-alkylthio, $(C_1$-$C_5)$-perfluoroalkyl, cyano, nitro, $NR^4R^5$, $COOR^6$, $(CO)NR^7R^8$ or a $(C_1$-$C_5$-alkylene)-O—(CO)-$(C_1$-$C_5)$alkyl group, preferably from the group $C_1$-$C_3$-alkyl, $C_1$-$C_3$-alkoxy, hydroxy, halogen, or carbonyl; preferably with methyl, chlorine or fluorine. The substituents can be the same or different.

The substituent carbonyl for a group $R^2$ is to be defined such that the carbonyl carbon atom is a ring carbon atom, to which an oxygen atom is double-bound.

Compounds of general formula I, in which radical $R^2$ is substituted with none, one or several of the same or different radicals from the group $C_1$-$C_3$-alkyl, $C_1$-$C_3$-alkoxy, hydroxy, halogen, or carbonyl, preferably with none or one or several of the same or different radicals from the group $C_1$-$C_3$-alkyl, hydroxy, carbonyl or halogen, in particular by one or more of the same or different radicals from the group methyl, chlorine or fluorine, especially by methyl, chlorine or fluorine, are a subject of the invention.

The nitrogen atom in the indazole, quinolone, isoquinolone and phthalazine of radical $R^2$ of general claim 1 can also be alkylated with a $C_1$-$C_3$-alkyl group.

Compounds of general formula I, in which $R^2$ means a monocyclic 5- or 6-membered heterocyclic ring system that is linked via any position, such as, e.g., furan or thiophene, are another subject of the invention.

Compounds of general formula I, in which $R^2$ means an optionally substituted phenyl ring or naphthyl ring, are another subject of the invention.

As substituents, the same that are already disclosed for the case that $R^1$ means phenyl, are suitable.

With a partially aromatic ring system, bicyclic systems are meant that contain an aromatic ring and a non-aromatic ring, such as, e.g., benzoxazinones or dihydroindolone.

Compounds according to claim 1, in which $R^3$ means trifluoromethyl or pentafluoroethyl, are a special subject of the invention. Compounds of general formula I, in which $R^1$ means a phenyl group, which optionally is substituted with 0-3 of the same or different substituents, selected from the group carbonyl, $C_1$-$C_3$-alkoxy, hydroxy, and halogen, in particular carbonyl, methoxy, hydroxy, fluorine, chlorine, or bromine, $R^2$ means dihydroisoindolonyl, isoquinolonyl, quinazolinyl, indazolyl, coumarinyl, isocoumarinyl, in particular dihydroisoindolonyl, isoquinolonyl, quinazolinyl, indazolyl, isocoumarinyl, phthalazinyl, quinolonyl group, which optionally can be substituted with 0-2 substituents that are selected from the group carbonyl, $C_1$-$C_3$-alkyl and halogen, in particular methyl and fluorine, and $R^3$ means $CF_3$ or $C_2F_5$, in particular $CF_3$, are a preferred subject of the invention.

In addition, the invention relates to the use of the compounds of general formula I for the production of pharmaceutical agents as well as their use for the production of pharmaceutical agents for treating inflammatory diseases.

The $C_1$-$C_5$-alkyl groups can be straight-chain or branched and stand for a methyl, ethyl, n-propyl, iso-propyl, n-butyl, iso-butyl, tert-butyl or n-pentyl group, or a 2,2-dimethylpropyl, 2-methylbutyl or 3-methylbutyl group. A methyl or ethyl group is preferred. They can optionally be substituted by 1-3 hydroxy, 1-3 $C_1$-$C_5$-alkoxy and/or 1-3 $COOR^6$ groups. Preferred are hydroxy groups.

$COOR^6$ can be free acid or a $C_1$-$C_5$-alkylester, whereby the alkyl radical is defined as already described above.

The $C_1$-$C_5$-alkoxy groups in $R^1$ and $R^2$ can be straight-chain or branched and stand for a methoxy, ethoxy, n-propoxy, iso-propoxy, n-butoxy, iso-butoxy, tert-butoxy or n-pentoxy, 2,2-dimethylpropoxy, 2-methylbutoxy or 3-methylbutoxy group. A methoxy or ethoxy group is preferred.

The $C_1$-$C_5$-alkylthio groups can be straight-chain or branched and stand for a methylthio, ethylthio, n-propylthio, iso-propylthio, n-butylthio, iso-butylthio, tert-butylthio or n-pentylthio, 2,2-dimethylpropylthio, 2-methylbutylthio or 3-methylbutylthio group. A methylthio or ethylthio group is preferred.

For a partially or completely fluorinated $C_1$-$C_3$-alkyl group, the following partially or completely fluorinated groups are considered: fluoromethyl, difluoromethyl, trifluoromethyl, fluoroethyl, 1,1-difluoroethyl, 1,2-difluoroethyl, 1,1,1-trifluoroethyl, tetrafluoroethyl, and pentafluoroethyl. Of the latter, the trifluoromethyl group or the pentafluoroethyl group is preferred.

The designation halogen atom or halogen means a fluorine, chlorine, bromine or iodine atom. Preferred is a fluorine, chlorine or bromine atom.

The $NR^4R^5$ group can mean, for example, $NH_2$, $N(H)CH_3$, $N(CH_3)_2$, $N(H)(CO)CH_3$, $N(CH_3)(CO)CH_3$, $N[(CO)CH_3]_2$, $N(H)CO_2CH_3$, $N(CH_3)CO_2CH_3$, or $N(CO_2CH_3)_2$.

The double bond in general formula I can be between atoms a and b or between atoms b and c.

Also, compounds that have a double bond neither between atoms a and b nor between atoms b and c are subjects of the invention.

The compounds of general formula I according to the invention can be present as stereoisomers because of the presence of asymmetry centers. Subjects of this invention are all possible diastereomers, both as racemates and in enantiomer-pure form.

The compounds according to the invention can also be present in the form of salts with physiologically compatible anions, for example in the form of hydrochlorides, sulfates, nitrates, phosphates, pivalates, maleates, fumarates, tartrates, benzoates, mesylates, citrates or succinates.

The compounds can be produced by the process that is described below.

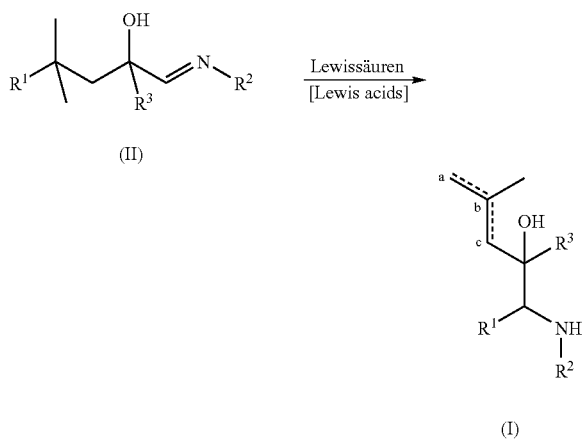

The compounds that are described in the application text are produced in the reaction of the corresponding imines with Lewis acids, especially in the reaction with boron tribromide in an organic solvent, preferably in a polar solvent, for example dichloromethane and subsequent conventional purification. The reaction is carried out in a temperature range of −70° C. to +30° C. (preferably −30° C. to +30° C.). The imines in turn are formed by the correspondingly described aldehydes being reacted with the desired amines in the conventional way. This takes place by reaction with titanates or by reaction in an acid medium or under approximately neutral conditions (for example THF/alcohol), either by stirring at room temperature or by boiling in a water separator.

If the compounds according to the invention are present as racemic mixtures, they can be separated into pure, optically active forms according to the methods of racemate separation that are familiar to one skilled in the art. For example, the racemic mixtures can be separated by chromatography on an even optically active carrier material (CHIRALPAK AD®) into the pure isomers. It is also possible to esterify the free hydroxy group in a racemic compound of general formula I with an optically active acid and to separate the diastereoisomeric esters that are obtained by fractionated crystallization or by chromatography, and to saponify the separated esters in each case to the optically pure isomers. As an optically active acid, for example, mandelic acid, camphorsulfonic acid or tartaric acid can be used.

The binding of the substances to the glucocorticoid receptor (GR) and other steroid hormone receptors (mineral corticoid receptor (MR), progesterone receptor (PR) and androgen receptor (AR)) is examined with the aid of recombinantly produced receptors. Cytosol preparations of Sf9 cells, which had been infected with recombinant baculoviruses, which code for the GR, are used for the binding studies. In comparison to reference substance [$^3$H]-dexamethasone, the substances show a high to very high affinity to GR. $IC_{50}$(GR)=64 nM was thus measured for the compound from Example 3.

As an essential, molecular mechanism for the anti-inflammatory action of glucocorticoids, the GR-mediated inhibition of the transcription of cytokines, adhesion molecules, enzymes and other pro-inflammatory factors is considered. This inhibition is produced by an interaction of the GR with other transcription factors, e.g., AP-1 and NF-kappa-B (for a survey, see Cato, A. C. B., and Wade, E., BioEssays 18, 371-378, 1996).

The compounds of general formula I according to the invention inhibit the secretion of cytokine IL-8 into the human monocyte cell line THP-1 that is triggered by lipopolysaccharide (LPS). The concentration of the cytokines was determined in the supernatant by means of commercially available ELISA kits. The compound from Example 3 showed an inhibition $IC_{50}$(IL8)=25 nmol.

The anti-inflammatory action of the compounds of general formula I was tested in the animal experiment by tests in the croton oil-induced inflammation in rats and mice (J. Exp. Med. (1995), 182, 99-108). To this end, croton oil in ethanolic solution was applied topically to the animals' ears. The test substances were also applied topically or systemically at the same time or two hours before the croton oil. After 16-24 hours, the ear weight was measured as a yardstick for inflammatory edema, the peroxidase activity as a yardstick for the invasions of granulocytes, and the elastase activity as a yardstick for the invasion of neutrophilic granulocytes. In this test, the compounds of general formula I inhibit the three above-mentioned inflammation parameters both after topical administration and after systemic administration.

One of the most frequent undesirable actions of a glucocorticoid therapy is the so-called "steroid diabetes" [cf., Hatz, H. J., Glucocorticoide: Immunologische Grundlagen, Pharmakologie und Therapierichtlinien [Glucocorticoids: Immunological Bases, Pharmacology and Therapy Guidelines], Wissenschaftliche Verlagsgesellschaft mbH, Stuttgart, 1998]. The reason for this is the stimulation of gluconeogenesis in the liver by induction of the enzymes responsible in this respect and by free amino acids, which are produced from the degradation of proteins (catabolic action of glucocorticoids). A key enzyme of the catabolic metabolism in the liver is tyrosinamino transferase (TAT). The activity of this enzyme can be determined from liver homogenates by photometry and represents a good measurement of the undesirable metabolic actions of glucocorticoids. To measure the TAT induction, the animals are sacrificed 8 hours after the test substances are administered, the livers are removed, and the TAT activity is measured in the homogenate. In this test, at doses in which they have an anti-inflammatory action, the compounds of general formula I induce little or no tyrosinamino transferase.

Because of their anti-inflammatory and, in addition, anti-allergic, immunosuppressive and antiproliferative action, the compounds of general formula I according to the invention can be used as medications for treatment or prophylaxis of the following pathologic conditions in mammals and humans: In this case, the term "DISEASE" stands for the following indications:

(i) Lung diseases that are accompanied by inflammatory, allergic and/or proliferative processes:
  Chronic, obstructive lung diseases of any origin, primarily bronchial asthma
  Bronchitis of different origins
  All forms of restrictive lung diseases, primarily allergic alveolitis,
  All forms of pulmonary edema, primarily toxic pulmonary edema
  Sarcoidoses and granulomatoses, especially Boeck's disease
(ii) Rheumatic diseases/autoimmune diseases/joint diseases that are accompanied by inflammatory, allergic and/or proliferative processes:
  All forms of rheumatic diseases, especially rheumatoid arthritis, acute rheumatic fever, polymyalgia rheumatica
  Reactive arthritis
  Inflammatory soft-tissue diseases of other origins
  Arthritic symptoms in the case of degenerative joint diseases (arthroses)
  Traumatic arthritides
  Collagenoses of any origin, e.g., systemic lupus erythematodes, sclerodermia, polymyositis, dermatomyositis, Sjögren's syndrome, Still's syndrome, Felty's syndrome
(iii) Allergies that are accompanied by inflammatory and/or proliferative processes:
  All forms of allergic reactions, e.g., Quincke's edema, hay fever, insect bites, allergic reactions to pharmaceutical agents, blood derivatives, contrast media, etc., anaphylactic shock, urticaria, contact dermatitis
(iv) Vascular inflammations (vasculitides)
  Panarteritis nodosa, temporal arteritis, erythema nodosum
(v) Dermatological diseases that are accompanied by inflammatory, allergic and/or proliferative processes:
  Atopic dermatitis (primarily in children)
  Psoriasis
  Pityriasis rubra pilaris
  Erythematous diseases, triggered by different noxae, e.g., radiation, chemicals, burns, etc.
  Bullous dermatoses
  Diseases of the lichenoid group,
  Pruritis (e.g., of allergic origin)
  Seborrheal eczema
  Rosacea
  Pemphigus vulgaris
  Erythema exudativum multiforme
  Balanitis
  Vulvitis
  Hair loss such as alopecia areata
  Cutaneous T-cell lymphoma
(vi) Kidney diseases that are accompanied by inflammatory, allergic and/or proliferative processes:
  Nephrotic syndrome
  All nephritides
(vii) Liver diseases that are accompanied by inflammatory, allergic and/or proliferative processes:
  Acute liver cell decomposition
  Acute hepatitis of different origins, e.g., viral, toxic, pharmaceutical agent-induced
  Chronic aggressive hepatitis and/or chronic intermittent hepatitis
(viii) Gastrointestinal diseases that are accompanied by inflammatory, allergic and/or proliferative processes:
  Regional enteritis (Crohn's disease)
  Colitis ulcerosa
  Gastritis
  Reflux esophagitis
  Ulcerative colitis of other origins, e.g., native sprue
(ix) Proctologic diseases that are accompanied by inflammatory, allergic and/or proliferative processes:
  Anal eczema
  Fissures
  Hemorrhoids
  Idiopathic proctitis
(x) Eye diseases that are accompanied by inflammatory, allergic and/or proliferative processes:
  Allergic keratitis, uveitis, iritis
  Conjunctivitis
  Blepharitis
  Optic neuritis
  Chorioiditis
  Sympathetic ophthalmia
(xi) Diseases of the ear-nose-throat area that are accompanied by inflammatory, allergic and/or proliferative processes:
  Allergic rhinitis, hay fever
  Otitis externa, e.g., caused by contact dermatitis, infection, etc.
  Otitis media
(xii) Neurological diseases that are accompanied by inflammatory, allergic and/or proliferative processes:
  Cerebral edema, primarily tumor-induced cerebral edema
  Multiple sclerosis
  Acute encephalomyelitis
  Meningitis
  Various forms of convulsions, e.g., infantile nodding spasms
(xiii) Blood diseases that are accompanied by inflammatory, allergic and/or proliferative processes:
  Acquired hemolytic anemia
  Idiopathic thrombocytopenia
(xiv) Tumor diseases that are accompanied by inflammatory, allergic and/or proliferative processes:
  Acute lymphatic leukemia
  Malignant lymphoma
  Lymphogranulomatoses
  Lymphosarcoma
  Extensive metastases, mainly in breast, bronchial and prostate cancers
(xv) Endocrine diseases that are accompanied by inflammatory, allergic and/or proliferative processes:
  Endocrine orbitopathy
  Thyreotoxic crisis
  De Quervain's thyroiditis
  Hashimoto's thyroiditis
  Basedow's disease
(xvi) Organ and tissue transplants, graft-versus-host disease
(xvii) Severe shock conditions, e.g., anaphylactic shock, systemic inflammatory response syndrome (SIRS)
(xviii) Substitution therapy in:
  Innate primary suprarenal insufficiency, e.g., congenital adrenogenital syndrome
  Acquired primary suprarenal insufficiency, e.g., Addison's disease, autoimmune adrenalitis, meta-infective tumors, metastases, etc.
  Innate secondary suprarenal insufficiency, e.g., congenital hypopituitarism
  Acquired secondary suprarenal insufficiency, e.g., meta-infective tumors, etc.

(xix) Vomiting that is accompanied by inflammatory, allergic and/or proliferative processes:
e.g., in combination with a 5-HT3 antagonist in cytostatic-agent-induced vomiting
(xx) Pains of inflammatory origins, e.g., lumbago.

Moreover, the compounds of general formula I according to the invention can be used for treatment and prophylaxis of additional pathologic conditions that are not mentioned above, for which synthetic glucocorticoids are now used (see in this respect Hatz, H. J., Glucocorticoide: Immunologische Grundlagen, Pharmakologie und Therapierichtlinien, Wissenschaftliche Verlagsgesellschaft mbH, Stuttgart, 1998).

All previously mentioned indications (i) to (xx) are described in more detail in Hatz, H. J., Glucocorticoide: Immunologische Grundlagen, Pharmakologie und Therapierichtlinien, Wissenschaftliche Verlagsgesellschaft mbH, Stuttgart, 1998.

For the therapeutic actions in the above-mentioned pathologic conditions, the suitable dose varies and depends on, for example, the active strength of the compound of general formula I, the host, the type of administration, and the type and severity of the conditions that are to be treated, as well as the use as a prophylactic agent or therapeutic agent.

In addition, the invention provides:
(i) The use of one of the compounds of formula I according to the invention or mixture thereof for the production of a medication for treating a DISEASE;
(ii) A process for treating a DISEASE, said process comprises an administration of an amount of the compound according to the invention, whereby the amount suppresses the disease and whereby the amount of compound is given to a patient who requires such a medication;
(iii) A pharmaceutical composition for treating a DISEASE, said treatment comprises one of the compounds according to the invention or mixture thereof and at least one pharmaceutical adjuvant and/or vehicle.

In general, satisfactory results can be expected in animals when the daily doses comprise a range of 1 µg to 100,000 µg of the compound according to the invention per kg of body weight. In the case of larger mammals, for example the human, a recommended daily dose lies in the range of 1 µg to 100,000 µg per kg of body weight. Preferred is a dose of 10 to 30,000 µg per kg of body weight, and more preferred is a dose of 10 to 10,000 µg per kg of body weight. For example, this dose is suitably administered several times daily. For treating acute shock (e.g., anaphylactic shock), individual doses can be given that are significantly above the above-mentioned doses.

The formulation of the pharmaceutical preparations based on the new compounds is carried out in a way that is known in the art by the active ingredient being processed with the vehicles that are commonly used in galenicals, fillers, substances that influence decomposition, binding agents, moisturizers, lubricants, absorbents, diluents, flavoring correctives, coloring agents, etc., and converted into the desired form of administration. In this case, reference is made to Remington's Pharmaceutical Science, 15$^{th}$ Edition, Mack Publishing Company, East Pennsylvania (1980).

For oral administration, especially tablets, coated tablets, capsules, pills, powders, granulates, lozenges, suspensions, emulsions or solutions are suitable.

For parenteral administration, injection and infusion preparations are possible.

For intra-articular injection, correspondingly prepared crystal suspensions can be used.

For intramuscular injection, aqueous and oily injection solutions or suspensions and corresponding depot preparations can be used.

For rectal administration, the new compounds can be used in the form of suppositories, capsules, solutions (e.g., in the form of enemas) and ointments both for systemic and for local treatment.

For pulmonary administration of the new compounds, the latter can be used in the form of aerosols and inhalants.

For local application to eyes, outer ear channels, middle ears, nasal cavities, and paranasal sinuses, the new compounds can be used as drops, ointments and tinctures in corresponding pharmaceutical preparations.

For topical application, formulations in gels, ointments, fatty ointments, creams, pastes, powders, milk and tinctures are possible. The dosage of the compounds of general formula I should be 0.01%-20% in these preparations to achieve a sufficient pharmacological action.

The invention also comprises the compounds of general formula I according to the invention as therapeutic active ingredients.

In addition, the compounds of general formula I according to the invention are part of the invention as therapeutic active ingredients together with pharmaceutically compatible and acceptable adjuvants and vehicles.

The invention also comprises a pharmaceutical composition that contains one of the pharmaceutically active compounds according to the invention or mixtures thereof or a pharmaceutically compatible salt thereof and a pharmaceutically compatible salt or pharmaceutically compatible adjuvants and vehicles.

Experiments

EXAMPLE 1

(rac.) 4-{[1-(4-Chloro-2-methoxyphenyl)-2-hydroxy-4-methyl-2-(trifluoromethyl)-pent-4-en-1-yl]amino}-6-fluoro-2,3-dihydroisoindol-1-one 4-Amino-6-fluoro-2,3-dihydroisoindol-1-one 2-Methyl-5-fluoro-3-nitrobenzoic Acid 116 ml of sulfuric acid is introduced and mixed in portions at −15° C. with 14.70 g (95.37 mmol) of 5-fluoro-2-methylbenzoic acid. A mixture of nitrating acid (4.79 ml of fuming nitric acid and 21.8 ml of concentrated sulfuric acid) is added in drops to this mixture, specifically at −15 to −10° C. for a period of 90 minutes. After three more hours of stirring, the reaction mixture is poured into ice water and stirred vigorously for about one-half hour. The precipitated crystallizate is suctioned off, washed neutral with water and dried. The yield is 8.56 g (45.1%) of a mixture of various regioisomers and by-products. This mixture is thus used in the next stage (esterification) and purified in this stage.

2-Methyl-5-fluoro-3-nitrobenzoic Acid Methyl Ester 8.56 g (42.99 mmol) of 2-methyl-5-fluoro-3-nitrobenzoic acid is added in 76 ml of N,N-dimethylformamide and mixed with 9.15 g (64.48 mmol) of methyl iodide and 8.91 g (64.48 mmol) of potassium carbonate. After 65 hours of stirring at room temperature, the reaction mixture is added to ice water and extracted several times with ethyl acetate. The combined organic extracts are washed with water and brine. After drying (sodium sulfate), desiccant is suctioned out, and the solvent is spun off. Repeated chromatography on silica gel (mobile solvent ethyl acetate/hexane) yields the desired compound, specifically in a yield of 25.9% (2.37 g).

$^1$H-NMR (300 MHz, CDCl$_3$): δ=2.60 (3H), 3.96 (3H), 7.61 (1H), 7.77 (1H).

2-(Bromomethyl)-5-fluoro-3-nitrobenzoic Acid Methyl Ester 2.37 g (11.12 mmol) of 5-fluoro-2-methyl-3-nitrobenzoic acid methyl ester is added into 35 ml of carbon tetrachloride, and mixed with 2.24 g (12.24 mmol) of N-bromosuccinimide and 5.4 mg of benzoyl peroxide. After four days of refluxing, and after cooling, the succinimide is suctioned off (glass-fiber filter), and then the filtrate is spun in to the dry state. Chromatography on a Flashmaster yields 2.47 g (75.9%) of the desired compound.

$^1$H-NMR (300 MHz, CDCl$_3$): δ=4.01 (3H), 5.13 (2H), 7.72 (1H), 7.87 (1H).

2-(Azidomethyl)-5-fluoro-3-nitrobenzoic Acid Methyl Ester 2.47 g (8.46 mmol) of 2-(bromomethyl)-5-fluoro-3-nitrobenzoic acid methyl ester is mixed with 8.3 ml of N,N-dimethylformamide and 5.5 ml of water. After 0.82 g (12.66 mmol) of sodium azide is added, the batch is stirred overnight. The reaction mixture is added to water and extracted three times with methyl tert-butyl ether. The combined organic extracts are washed with water and with brine. After being dried on sodium sulfate, it is filtered, and the solvent is spun off. Chromatography on a Flashmaster yields 2.06 g (95.8%) of the desired azide.

$^1$H-NMR (300 MHz, CDCl$_3$): δ=4.00 (3H), 4.90 (2H), 7.73 (1H), 7.87 (1H).

4-Amino-6-fluoro-2,3-dihydroisoindol-1-one 1.86 g (7.32 mmol) of 2-(azidomethyl)-5-fluoro-3-nitrobenzoic acid methyl ester is added into 46 ml of ethanol and 3.4 ml of glacial acetic acid, and it is mixed with 256.6 mg of Pd/C. After stirring overnight at room temperature under hydrogen atmosphere, the catalyst is suctioned off with a glass-fiber filter, and the filtrate is evaporated to the dry state. The residue, 1.18 mg (97.5%) of the desired compound, is further used in crude form.

$^1$H-NMR (300 MHz, DMSO-d$_6$): δ=4.10 (2H), 5.75 (2H), 6.46-6.57 (2H), 8.50 (1H).

4-(4-Chloro-2-methoxyphenyl)-2-hydroxy-4-methyl-2-(trifluoromethyl)pentan-1-ol

A solution of 3 g of 2-hydroxy-4-methylene-2-(trifluoromethyl)valeric acid ethyl ester in 22 ml of 3-chloroanisole is mixed at room temperature in portions with aluminum trichloride. After 48 hours of stirring at room temperature, the batch is mixed with 2N hydrochloric acid and hexane, and it is stirred for another hour. After washing with 2N hydrochloric acid and water, excess 3-chloroanisole is distilled off in a vacuum. The remaining residue is purified by chromatography on silica gel (mobile solvent: hexane/ethyl acetate). 2.85 g of a mixture of 4-(4-chloro-2-methoxyphenyl)-2-hydroxy-4-methyl-2-(trifluoromethyl)valeric acid ethyl ester and the regioisomeric compound 4-(2-chloro-4-methoxyphenyl)-2-hydroxy-4-methy-2-(trifluoromethyl)valeric acid ethyl ester is obtained as a yellow oil. This substance mixture is mixed in 90 ml of ether at 0° C. with 445 mg of lithium aluminum hydride and stirred for 12 hours. The batch is added to saturated sodium bicarbonate solution and filtered through diatomaceous earth. The phases are separated, and the aqueous phase is extracted with ethyl acetate. It is washed with water and brine, dried with sodium sulfate and concentrated by evaporation in a vacuum. After chromatography on silica gel (mobile solvent hexane/ethyl acetate), 1.87 g of the desired compound 4-(4-chloro-2-methoxyphenyl)-2-hydroxy-4-methyl-2-(trifluoromethyl)pentan-1-ol as a 1st fraction, and 160 mg of the regioisomeric compound 4-(2-chloro-4-methoxyphenyl)-2-hydroxy-4-methyl-2-(trifluoromethyl)pentan-1-ol as a 2nd fraction are obtained as colorless oils.

1st Fraction: $^1$H-NMR (300 MHz, CDCl$_3$), δ=1.41 (s, 3H), 1.51 (s, 3H), 2.24 (d, 1H), 2.51 (d, 1H), 2.84 (bs, 1H), 3.36 (d, 1H), 3.48 (d, 1H), 3.85 (s, 3H), 6.88 (d, 1H), 6.92 (dd, 1H), 7.24 (d, 1H)

2nd Fraction: $^1$H-NMR (300 MHz, CDCl$_3$), δ=1.52 (s, 3H), 1.62 (s, 3H), 2.18 (d, 1H), 2.76 (d, 1H), 2.93 (bs, 1H), 3.33 (d, 1H), 3.55 (d, 1H), 3.80 (s, 3H), 6.78 (dd, 1H), 6.90 (d, 1H), 7.38 (d, 1H)

4-(4-Chloro-2-methoxyphenyl)-2-hydroxy-4-methyl-2-(trifluoromethyl)pentanal 854.6 mg (6.733 mmol) of oxalyl chloride in 14.5 ml of dichloromethane is introduced into a heated flask. At −70° C., 1.05 ml of DMSO, dissolved in 3 ml of dichloromethane, is added in drops, and the batch is stirred for five more minutes. Then, 2 g (6.12 mmol) of 4-(4-chloro-2-methoxyphenyl)-2-hydroxy-4-methyl-2-trifluoromethyl-pentan-1-ol, dissolved in six milliliters of dichloromethane, is added in drops. After 20 minutes of stirring, the batch is carefully mixed with 4.24 ml (30.61 mmol) of triethylamine, specifically in a temperature range of between −70 and −60° C. After five minutes of stirring at −70° C., the reaction mixture is allowed to slowly reach room temperature. 25 ml of water is added, and the batch is stirred for one more hour at room temperature. After phase separation, the aqueous phase is shaken once with 100 ml of dichloromethane. The combined organic extracts are washed with 1% sulfuric acid, 5% sodium bicarbonate solution and brine. According to the conventional procedures, 1.92 g (96.9%) of the desired aldehyde is obtained, which is incorporated in crude form into the next stage.

$^1$H-NMR (300 MHz, CDCl$_3$): δ=1.37 (3H), 1.45 (3H), 2.22 (1H), 3.35 (1H), 3.59 (1H), 3.90 (3H), 6.80-6.92 (2H), 7.04 (1H), 9.02 (1H).

4-{[4-(4-Chloro-2-methoxyphenyl)-2-hydroxy-4-methyl-2-trifluoromethyl)pentylidene]amino}6-fluoro-2,3-dihydroisoindol-1-one 250 mg (0.769 mmol) of rac-4-(4-chloro-2-methoxyphenyl)-2-hydroxy-4-methyl-2-(trifluoromethyl)-pentanal is stirred for four days at room temperature with 127.9 mg (0.769 mmol) of 4-amino-6-fluoro-2,3-dihydroisoindol-1-one in 1.12 ml of glacial acetic acid. The mixture is mixed three times with toluene and evaporated to the dry state in a rotary evaporator. The residue is chromatographed on silica gel (mobile solvent ethyl acetate/hexane). 236.7 mg (65%) of the desired compound is isolated.

$^1$H-NMR (300 MHz, CDCl$_3$): δ=1.38 (3H), 1.53 (3H), 2.21 (1H), 3.40 (1H), 3.90 (3H), 4.30 (2H), 4.54 (1H), 6.22 (1H), 6.70 (1H), 6.78 (1H), 6.89 (1H), 7.04 (1H), 7.45 (1H), 7.49 (1H).

4-{[1-(4-Chloro-2-methoxyphenyl)-2-hydroxy-4-methyl-2-(trifluoromethyl)-pent-4-en-1-yl]amino}-6-fluoro-2,3-dihydroisoindol-1-one)

145 mg (0.307 mmol) of 4-{[4-(4-chloro-2-methoxyphenyl)-2-hydroxy-4-methyl-2-trifluoromethyl)pentylidene]amino}6-fluoro-2,3-dihydroisoindol-1-one is mixed at −30° C. with 6.1 ml of a 1 M solution of BBr$_3$ in dichloromethane and stirred for one and a half hours at −20° C. The reaction mixture is mixed drop by drop at −20° C. with saturated sodium bicarbonate solution until a pH of 8 is reached. After mixing with ethyl acetate, the cold bath is removed and stirred for 15 minutes. After extraction with ethyl acetate (twice), the combined organic extracts are washed with water and brine and dried (sodium sulfate). After the desiccant is filtered off and after the solvent is spun off, the residue is chromatographed on silica gel (mobile solvent methanol/dichloromethane). 25 mg (17.2%) of the desired compound is isolated.

$^1$H-NMR (300 MHz, CD$_3$OD): δ=1.78 (3H), 2.22 (1H), 2.48 (1H), 4.02 (3H), 4.22-4.43 (2H), 4.67 (1H), 4.82 (1H), 5.25 (1H), 6.31 (1H), 6.71 (1H), 6.99 (1H), 7.10 (1H), 7.52 (1H).

EXAMPLE 2

4-{[1-(5-Chloro-2-hydroxyphenyl)-2-hydroxy-4-methyl-2-(trifluoromethyl-pent-4-en-1-yl]amino}-6-fluoro-2,3-dihydroisoindol-1-one

4-{[4-(5-Chloro-2-methoxyphenyl)-2-hydroxy-4-methyl-2-trifluoromethyl)pentylidene]amino}6-fluoro-2,3-dihydroisoindol-1-one 250 mg (0.769 mmol) of rac-4-(5-chloro-2-methoxyphenyl)-2-hydroxy-4-methyl-2-(trifluoromethyl)-pentanal is stirred for four days at room temperature with 127.9 mg (0.769 mmol) of 4-amino-6-fluoro-2,3-dihydroisoindol-1-one in 1.12 ml of glacial acetic acid. The mixture is mixed three times with toluene and concentrated by evaporation in a rotary evaporator until a dry state is reached. The residue is chromatographed on silica gel (mobile solvent ethyl acetate/hexane). 244.8 mg (67.2%) of the desired compound is isolated.

$^1$H-NMR (300 MHz, CDCl$_3$): δ=1.38 (3H), 1.53 (3H), 2.20 (1H), 3.49 (1H), 3.89 (3H), 4.38 (2H), 4.60 (1H), 6.26 (1H), 6.68-6.80 (2H), 6.95 (1H), 7.02 (1H), 7.39-7.48 (2H).

4-{[1-(5-Chloro-2-hydroxyphenyl)-2-hydroxy-4-methyl-2-(trifluoromethyl)-pent-4-en-1-yl]amino}-6-fluoro-2,3-dihydroisoindol-1-one 140 mg (0.296 mmol) of 4-{[4-(5-chloro-2-methoxyphenyl)-2-hydroxy-4-methyl-2-trifluoromethyl)pentylidene]amino}6-fluoro-2,3-dihydroisoindol-1-one is mixed with 2.96 ml of a 1 M solution of BBr$_3$ in dichloromethane and stirred for 20 hours at room temperature. After the working-up that is described in Example 1, the residue is chromatographed with the aid of a Flashmaster (mobile solvent methanol/dichloromethane). 71 mg (52.3%) of the desired compound is isolated.

$^1$H-NMR (300 MHz, CD$_3$OD): δ=1.78 (3H), 2.25 (1H), 2.59 (1H), 4.42-4.45 (2H), 4.69 (1H), 4.82 (1H), 5.22 (1H), 6.47 (1H), 6.73 (1H), 6.87 (1H), 7.13 (1H), 7.48 (1H).

EXAMPLE 3

5-{[1-(5-Bromo-2-hydroxyphenyl)-2-hydroxy-4-methyl-2-(trifluoromethyl)-pent-4-en-1-yl]amino}-isoquinolin-1(2H)-one

5-Amino-isoquinolin-1(2H)-one

5-Nitroisocoumarin 16.4 g (84.03 mmol) of 2-methyl-3-nitrobenzoic acid methyl ester that is described under Example 1 is stirred with 26.8 g (225.1 mmol) of N,N-dimethylformamide dimethylacetal in 85 ml of dimethylformamide for 12 hours at 130° C. The solvent is drawn off in a rotary evaporator, the residue is taken up in methyl tert-butyl ether, and it is washed three times with water. After washing with saturated NaCl solution, the organic phase is dried. After the dessicant is filtered off and after the solvent is spun off, the remaining residue is chromatographed on silica gel (mobile solvent ethyl acetate/hexane). 8.73 g (54.5%) of the desired compound is isolated.

$^1$H-NMR (300 MHz, CDCl$_3$): δ=7.39 (1H), 7.45 (1H), 7.68 (1H), 8.49 (1H), 8.65 (1H).

5-Nitroisoquinolin-1(2H)-one 2.51 g (13.13 mmol) of 5-nitroisocoumarin is added into 100 ml of ethanol. Ammonia is pressure-forced in in an autoclave. The product precipitates and is suctioned off. 1.98 g (79.7%) of the desired compound is isolated.

$^1$H-NMR (300 MHz, DMSO-d$_6$): δ=6.97 (1H), 7.45 (1H), 7.65 (1H), 8.43 (1H), 8.57 (1H), 11.5 (1H).

5-Aminoisoquinolin-1(2H)-one 268.3 mg (1.51 mmol) of 5-nitroisoquinolin-1(2H)-one is added with 376.5 mg of ammonium chloride and 2.6 ml of water in 14 ml of ethanol and 5.4 ml of tetrahydrofuran. After the addition of 1.23 g of zinc powder in portions (heating to 30 to 35° C.), it is stirred for two hours. The reaction mixture is suctioned off through a glass-fiber filter and rewashed with ethyl acetate. After the filtrate is washed with water and saturated sodium chloride solution, the organic phase is dried as usual. Filtering-off of the desiccant and spinning-off of the solvent yield 196.5 mg (88.1%) of the desired amine.

$^1$H-NMR (300 MHz, DMSO-d$_6$): δ=5.6 (2H), 6.68 (1H), 6.87.45 (1H), 7.00 (1H), 7.17 (1H), 7.39 (1H), 11.7 (1H).

5-{[4-(5-Bromo-2-methoxyphenyl)-2-hydroxy-4-methyl-2-(trifluoromethyl)-pentylidene]amino}-isoquinolin-1(2H)-one 400 mg (1.297 mmol) of rac-4-(5-bromo-2-methoxyphenyl)-2-hydroxy-4-methyl-2-trifluoromethyl)-pentanal is stirred in 1.57 ml of glacial acetic acid with 173.5 mg (1.083 mmol) of 5-aminoisoquinolin-1(2H)-one for six days at room temperature. The mixture is mixed three times with toluene and evaporated to the dry state in a rotary evaporator. The residue is chromatographed on silica gel (mobile solvent ethyl acetate/hexane). 195 mg (35.2%) of the desired compound is isolated.

$^1$H-NMR (300 MHz, CDCl$_3$): δ=1.38 (3H), 1.53 (3H); 2.29 (1H), 3.50 (1H), 3.83 (1H), 4.83 (1H); 6.50-6.62 (2H), 6.75 (1H), 7.04 (1H), 7.16 (1H), 7.19-7.30 (1H), 7.31-7.43 (2H), 8.32 (1H), 10.83 (1H).

5-{[1-(5-Bromo-2-hydroxyphenyl)-2-hydroxy-4-methyl-2-(trifluoromethyl)-pent-4-en-1-yl]amino}-isoquinolin-1(2H)-one 195 mg (0.381 mmol) of 5-{[4-(5-bromo-2-methoxyphenyl)-2-hydroxy-4-methyl-2-(trifluoromethyl)pentylidene]amino}-isoquinolin-1(2H)-one is mixed with 3.8 ml of a 1 M solution of BBr$_3$ in dichloromethane and stirred for 90 minutes at room temperature. The reaction mixture is added to ice, brought to a pH of 8 with sodium bicarbonate solution and further worked up as described in Example 1. Together with the residue from another batch, in which 145 mg (0.283 mmol) of rac-5-{[E/Z]-[4-(5-bromo-2-methoxyphenyl)-2-hydroxy-4-methyl-2-(trifluoromethyl)pentylidene]amino}-isoquinolin-1(2H)-one had been used, the residue is chromatographed with the aid of a Flashmaster (amine phase; mobile solvent dichloromethane/methanol). 45.1 mg (13.64%) of the desired compound is isolated.

$^1$H-NMR (300 MHz, CD$_3$OD): δ=1.80 (3H), 2.39 (1H), 2.60 (1H), 4.68 (1H), 4.82 (1H), 5.22 (1H), 6.63-6.89 (3H), 7.12-7.30 (3H), 7.50 (1H), 7.60 (1H).

EXAMPLE 4

(rac.) 4-{[1-(5-Fluoro-2-hydroxyphenyl)-2-hydroxy-4-methyl-2-(trifluoromethyl)-pent-4-en-1-yl]amino}-2,3-dihydroisoindol-1-one and (rac.) 4-{[1-(5-Fluoro-2-hydroxyphenyl)-2-hydroxy-4-methyl-2-(trifluoromethyl)-pent-3-en-1-yl]amino}-2,3-dihydroisoindol-1-one

4-(5-Fluoro-2-methoxyphenyl)-2-hydroxy-4-methyl-2-trifluoromethyl)-pentanal 6.55 g (21.11 mmol) of rac-4-(5-fluoro-2-methoxyphenyl)-2-hydroxy-4-methyl-2-trifluoromethyl)-pentan-1-ol (Name) (WO 00/32584) is dissolved in 224 ml of dichloromethane and mixed at room temperature with 74 ml of dry dimethyl sulfoxide and 10.68 g (105.55 mmol) of triethylamine. At 15 to 18° C., 10.08 g (63.33 mmol) of the SO$_3$/pyridine complex is added in portions within 40 minutes. After stirring overnight at room temperature, 84 ml of saturated ammonium chloride solution is added. Slight heating occurs. After 15 minutes of stirring at room temperature, it is extracted twice with 300 ml of diethyl ether each. The organic phases are washed with water and brine and dried (sodium sulfate). After the solvent is filtered off and after the solvent is spun off, the remaining residue is chromatographed on silica gel (mobile solvent ethyl acetate/hexane). 5.85 g (90%) of the desired compound is isolated.

$^1$H-NMR (300 MHz, CDCl$_3$): δ=1.40 (3H), 1.46 (3H), 2.22 (1H), 3.38 (1H), 3.59 (1H), 3.86 (1H), 6.70-6.80 (1H), 6.82-6.97 (2H), 9.05 (1H).

4-{[4-(5-Fluoro-2-methoxyphenyl)-2-hydroxy-4-methyl-2-(trifluoromethyl)-pentylidene]amino}2,3-dihydroisoindol-1-one 400 mg (1.297 mmol) of 4-(5-fluoro-2-methoxyphenyl)-2-hydroxy-4-methyl-2-trifluoromethyl)-pentanal is stirred with 192.1 mg (1.297 mmol) of 4-amino-2,3-dihydroisoindol-1-one in 1.89 ml of glacial acetic acid for four days at room temperature. The mixture is mixed three times with toluene and evaporated to the dry state in a rotary evaporator. The residue is chromatographed on silica gel (mobile solvent ethyl acetate/hexane). 429.7 mg (75.5%) of the desired compound is isolated.

$^1$H-NMR (300 MHz, CDCl$_3$): δ=1.37 (3H), 1.52 (3H), 2.22 (1H), 3.42 (1H), 3.84 (3H), 4.37 (2H), 4.68 (1H), 6.53-6.68 (3H), 6.72-6.95 (2H), 7.37 (1H), 7.49 (1H), 7.75 (1H).

4-{[1-(5-Fluoro-2-hydroxyphenyl)-2-hydroxy-4-methyl-2-(trifluoromethyl)-pent-4-en-1-yl]amino}-2,3-dihydroisoindol-1-one 420 mg (0.958 mmol) of the compound 4-{[4-(5-fluoro-2-methoxyphenyl)-2-hydroxy-4-methyl-2-(trifluoromethyl)pentylidene]amino}2,3-dihydroisoindol-1-one that is described in the preceding paragraph is mixed with 9.6 ml of a 1 M solution of boron tribromide in dichloromethane and stirred for three-quarters of an hour at room temperature. The reaction mixture is mixed drop by drop at −30° C. with saturated sodium bicarbonate until a pH of 8 is reached. After dilution with ethyl acetate, the cold bath is removed, and it is vigorously stirred for 15 minutes. After being extracted twice with ethyl acetate, the organic phases are washed with water and saturated sodium chloride solution. After sodium sulfate is dried and after the solvent is spun off, the residue is chromatographed on a Flashmaster (silica gel, Flash NH$_2$) (mobile solvent dichloromethane/methanol). 37.8 mg (9.3%) of the desired compound is isolated.

$^1$H-NMR (300 MHz, CD$_3$OD): δ=1.82 (3H), 2.38 (1H), 2.55 (1H), 4.28-4.50 (2H), 4.69 (1H), 4.81 (1H), 5.20 (1H), 6.70-6.87 (3H), 7.06-7.17 (2H), 7.22 (1H).

In addition, 12.8 mg of the regioisomeric compound 4-{[1-(5-fluoro-2-hydroxyphenyl)-2-hydroxy-4-methyl-2-(trifluoromethyl)-pent-3-en-1-yl]amino}-2,3-dihydroisoindol-1-one is isolated.

Melting point: 195-197° C.

EXAMPLE 5

(rac.) 4-{[1-(5-Fluoro-2-hydroxyphenyl)-2-hydroxy-4-methyl-2-(trifluoromethyl)-pent-4-en-1-yl]amino}-6-fluoro-2,3-dihydroisoindol-1-one

4-{[4-(5-Fluoro-2-methoxyphenyl)-2-hydroxy-4-methyl-2-(trifluoromethyl)pentylidene]amino}6-fluoro-2,3-dihydroisoindol-1-one 380 mg (0.832 mmol) of the rac-4-(5-fluoro-2-methoxyphenyl)-2-hydroxy-4-methyl-2-trifluoromethyl)-pentanal that is described in Example 4 is reacted in 1.89 ml of glacial acetic acid with 215.4 mg (1.297 mmol) of the 4-amino-6-fluoro-2,3-dihydroisoindol-1-one that is described in Example 1, and it is stirred for 4 days at room temperature. Since starting material is still present according to TLC, the reaction mixture is mixed with toluene and boiled for 20 hours in a water separator. The toluene is drawn off in a rotary evaporator, and the residue is chromatographed on silica gel (mobile solvent ethyl acetate/hexane). 383.4 mg (64.7%) of the desired imine is isolated.

$^1$H-NMR (300 MHz, CDCl$_3$): δ=1.37 (3H), 1.53 (3H), 2.20 (1H), 3.47 (1H), 3.88 (3H), 4.32 (2H), 4.57 (1H), 6.22 (1H), 6.63-6.88 (4H), 7.42 (1H), 7.48 (1H).

4-{[1-(5-Fluoro-2-hydroxyphenyl)-2-hydroxy-4-methyl-2-(trifluoromethyl)-pent-4-en-1-yl]amino}-6-fluoro-2,3-dihydroisoindol-1-one 380 mg (0.832 mmol) of 4-{[4-(5-fluoro-2-methoxyphenyl)-2-hydroxy-4-methyl-2-(trifluoromethyl)pentylidene]amino}6-fluoro-2,3-dihydroisoindol-1-one is mixed at room temperature with 8.3 ml of a 1 M solution of BBr$_3$ in dichloromethane and stirred for one hour at ice bath temperature.

The working-up of the batch is carried out as described in Example 4. After the crude product is chromatographed on a Flashmaster (amine phase; mobile solvent methanol/dichloromethane), 22.2 mg (6.03%) of the desired compound is obtained.

$^1$H-NMR (300 MHz, CD$_3$OD): δ=1.80 (3H), 2.30 (1H), 2.55 (1H), 4.22-4.48 (2H), 4.68 (1H), 4.81 (1H), 5.17 (1H), 6.49 (1H), 6.72 (1H), 6.75-6.90 (2H), 7.17 (1H).

EXAMPLE 6

2-{4-Chloro-alpha-[(2-methylquinazolin-5-yl)amino]-2-methoxybenzyl}-1,1,1-trifluoro-4-methyl-pent-4-en-2-ol and 2-{4-Chloro-alpha-[(2-methylquinazolin-5-yl)amino]-2-methoxybenzyl}-1,1,1-trifluoro-4-methyl-pent-3-en-2-ol 5-Amino-2-methyquinazoline 12.7 g (mmol) of 2-methyl-5-nitro-3H-quinazolin-4-one (M. T. Bogert, V. J. Chambers *J. Org. Chem.* 1905, 649-658) and 37.5 g of phosphorus pentachloride are refluxed in 75 ml of phosphoryl chloride over 20 hours. After cooling, it is poured into saturated NaHCO$_3$ solution and extracted with ethyl acetate. The organic phase is dried, and the solvent is removed. 14 g of 4-chloro-2-methyl-5-nitroquinazoline, of which 4.5 g (20.2 mmol) in 225 ml of ethyl acetate and 22.5 ml of triethylamine are dissolved, is obtained. 2 g of palladium on carbon is added, and it is stirred for four hours under hydrogen atmosphere at normal pressure while being cooled with ice. Catalyst is removed from the solution by means of filtration over Celite, whereby it is rewashed with 200 ml of ethanol and concentrated by evaporation. After chromatography on silica gel with ethyl acetate-ethanol (0-10%), 530 mg of the product is obtained.

$^1$H-NMR (300 MHz, CDCl$_3$); δ=2.87 (s, 3H), 4.52 (br., 2H), 6.77 (d, 1H), 7.33 (d, 1H), 7.65 (t, 1H), 9.40 (s, 1H).

1,1,1,-Trifluoro-4-(4-chloro-2-methoxyphenyl)-2-[(E/Z)-(2-methyl-quinazol-5-yl)iminomethyl]-4-methyl-pentan-2-ol 325 mg (1.00 mmol) of rac-4-(4-chloro-2-methoxyphenyl)-2-hydroxy-4-methyl-2-(trifluoromethyl)-pentanal is dissolved with 200 mg (1.25 mmol) of 5-amino-2-methylquinazoline in 5 ml of toluene, and 0.74 ml (2.50 mmol) of titanium tetraisopropylate is added at room temperature. The mixture is stirred for 3 hours at 105° C. After cooling, the mixture is added to water, stirred for several minutes, suctioned off on diatomaceous earth, rewashed with ethyl acetate, and the phases are separated. The aqueous phase is extracted several times with ethyl acetate, and the combined organic phases are washed with saturated NaCl solution and dried with sodium sulfate. The solvent is removed in a rotary evaporator, and the crude product is chromatographed on silica gel (eluant: hexane/ethyl acetate 4:1). 130 mg (28%) of the desired compound is isolated.

(rac.) 2-{4-Chloro-alpha-[(2-methylquinazolin-5-yl)amino]-2-methoxybenzyl}-1,1,1-trifluoro-4-methyl-pent-4-en-2-ol 130 mg (0.28 mmol) of 1,1,1,-trifluoro-4-(4-chloro-2-methoxyphenyl)-2-[(2-methyl-quinazol-5-yl)iminomethyl]-4-methyl-pentan-2-ol is introduced into 5 ml of dichloromethane, and 5.6 ml of a 1 M solution of boron tribromide in dichloromethane is added in drops at −70° C. It is allowed to reach −10° C. within 1.5 hours, then 5 ml of a saturated NaHCO$_3$ solution is added, the phases are separated, the aqueous phase is extracted with dichloromethane, the combined organic phases are washed with saturated NaHCO$_3$ solution and saturated NaCl solution and dried with sodium sulfate. After the solvent is removed in a rotary evaporator, the crude product is chromatographed on silica gel (eluant: dichloromethane/methanol 98:2). 80 mg (62%) of the desired product is obtained as a yellow solid.

Melting point: 193° C.

Moreover, as a slightly more polar by-product, 7 mg of the double-bond-isomeric compound 2-{4-chloro-alpha-[(2-methylquinazolin-5-yl)amino]-2-methoxybenzyl}-1,1,1-trifluoro-4-methylpent-3-en-2-ol is obtained.

$^1$H-NMR (300 MHz, CD$_3$OD): δ=1.35 (s, 3H), 1.61 (s, 3H), 2.80 (s, 3H), 3.98 (s, 3H), 5.24 (s, 1H), 5.35 (s, 1H), 6.35 (d, J=8 Hz, 1H), 6.87 (dd, J=2/8 Hz, 1H), 6.97 (d, J=2 Hz, 1H), 7.09 (d, J=8 Hz, 1H), 7.49 (d, J=8 Hz, 1H), 7.60 (dd, J=8/8 Hz, 1H), 9.58 (s, 1H).

EXAMPLE 7

(rac.) 2-{4-Chloro-alpha-[(8-fluoro-2-methylquinazolin-5-yl)amino]-2-methoxybenzyl}-1,1,1-trifluoro-4-methylpent-4-en-2-ol and (rac.) 2-{4-Chloro-alpha-[(8-fluoro-2-methylquinazolin-5-yl)amino]-2-methoxybenzyl}-1,1,1-trifluoro-4-methylpent-3-en-2-ol 5-Amino-8-fluoro-2-methylquinazoline A solution of 2.4 g (18.6 mmol) of 2,5-difluoroaniline in 11 ml of water and 1.6 ml of concentrated hydrochloric acid (37%) that is 50° C. is added to a solution of 3.35 g (20.25 mmol) of chloral hydrate and 21.27 g (149.7 mmol) of sodium sulfate in 72 ml of water, which was stirred in advance for 1 hour at this temperature. It is stirred for another 30 minutes at room temperature, and after 4.09 g (58.9 mmol) of hydroxyl ammonium chloride in 19 ml of water is added, it is heated for 45 minutes to 125° C. and kept at this temperature for 5 minutes. After cooling and after another hour, the precipitated light-brown precipitate is filtered off, washed with water and dried. 3.0 g (15.0 mmol) of the hydroxylimine is obtained as an intermediate product, which is dissolved in portions in 15 ml of concentrated sulfuric acid at 60° C. After the addition is completed, it is heated for 2 hours to 80° C. and for 4 hours to 90° C. It is allowed to cool off, and the solution is poured onto 100 g of ice. It is extracted with ethyl acetate, the organic phase is washed with water, dried on sodium sulfate and concentrated by evaporation. After chromatography on silica gel with hexane-ethyl acetate (0-45%), 1.2 g (7.1 mmol) of the 4,7-difluoroisatin is obtained. 1.8 ml of a 30% hydrogen peroxide solution is added in drops to the isatin in 30 ml of a 1 molar sodium hydroxide solution over 10 minutes. After 2 hours of stirring at room temperature, it is cooled to 0° C., and 5 ml of a 4 molar hydrochloric acid is added and diluted with 50 ml of water. It is extracted with ethyl acetate, dried on sodium sulfate, concentrated by evaporation, and 1.27 g of the 3,6-difluoroanthranilic acid, which is reacted without further purification, is thus obtained quantitatively.

The 3,6-difluoroanthranilic acid is heated in 8 ml of acetic acid anhydride for 45 minutes to 100° C. After cooling, the acetic acid that is produced and excess acetic acid anhydride are removed azeotropically with toluene in a vacuum. The residue is mixed with 40 ml of a 25% ammonia solution while being cooled with ice, and it is stirred for 72 hours. It is diluted with water and acidified with acetic acid. It is extracted with ethyl acetate, the organic phase is washed with water, dried on sodium sulfate and concentrated by evaporation. The thus obtained 1.03 g (5.25 mmol) of 5,8-difluoro-2-methyl-3H-quinazolin-4-one and 6 g of phosphorus pentachloride are heated in 20 ml of phosphoryl chloride over 12 hours to 125° C. After cooling, it is poured into saturated $NaHCO_3$ solution and extracted with ethyl acetate. The organic phase is dried, and the solvent is removed. 1.7 g of 4-chloro-5,8-difluoro-2-methylquinazoline, which is dissolved in 60 ml of ethyl acetate and 5 ml of triethylamine, is obtained quantitatively. 600 mg of palladium on carbon is added, and it is shaken for 2 hours (480 ml of hydrogen absorption) under hydrogen atmosphere at normal pressure. Catalyst is removed from the solution by means of filtration on Celite, whereby it was rewashed with 100 ml of ethanol and concentrated by evaporation. After chromatography on silica gel with hexane-ethyl acetate-ethanol (0-40%), 550 mg of 5,8-difluoro-2-methylquinazoline is obtained. 890 mg (13.7 mmol) of sodium azide is added to 240 mg (1.3 mmol) of 5,8-difluoro-2-methylquinazoline, 300 mg (1.13 mmol) of 18-crown-6 in 10 ml of DMF, and the mixture is heated for 8 hours to 125° C. The solvent is removed in a vacuum and chromatographed on silica gel with ethyl acetate, and 52 mg of product is obtained.

$^1$H-NMR (300 MHz, $CDCl_3$); δ=2.92 (s, 3H), 4.31 (br., 2H), 6.67 (dd, 1H), 7.38 (dd, 1H), 9.37 (s, 1H).

(rac) 1,1,1,-Trifluoro-4-(4-chloro-2-methoxyphenyl)-2-[(8-fluoro-2-methyl-quinazol-5-yl)iminomethyl]-4-methyl-pentan-2-ol 2.40 g (7.39 mmol) of rac-4-(4-chloro-2-methoxyphenyl)-2-hydroxy-4-methyl-2-(trifluoromethyl)-pentanal is dissolved with 1.30 g (7.34 mmol) of 5-amino-8-fluoro-2-methylquinazoline in 30 ml of toluene, and 3.10 ml (14.7 mmol) of titanium tetraethylate is added at room temperature. The mixture is stirred for 3 hours at 105° C. After cooling, the mixture is added to water, stirred for several minutes, suctioned off on diatomaceous earth, rewashed with ethyl acetate and water, and the phases are separated. The aqueous phase is extracted several times with ethyl acetate, and the combined organic phases are washed with saturated NaCl solution and dried with sodium sulfate. The solvent is removed in a rotary evaporator, and the crude product is chromatographed on silica gel (eluant hexane/ethyl acetate 4:1). 3.20 g (90%) of the desired compound is isolated.

(rac.) 2-{4-Chloro-alpha-[(8-fluoro-2-methylquinazolin-5-yl)amino]-2-methoxybenzyl}-1,1,1-trifluoro-4-methylpent-4-en-2-ol 3.1 g (6.4 mmol) of (rac) 1,1,1,-trifluoro-4-(4-chloro-2-methoxyphenyl)-2-[(8-fluoro-2-methyl-quinazol-5-yl)iminomethyl]-4-methyl-pentan-2-ol is introduced into 50 ml of dichloromethane and 128 ml of a 1 M solution of boron tribromide in dichloromethane is added in drops at −75° C. It is allowed to reach −20° C. within 2.5 hours. Then, the reaction mixture is added to 300 ml of a saturated $NaHCO_3$ solution, stirred for 15 more minutes, the phases are separated, the aqueous phase is extracted with dichloromethane, the combined organic phases are washed with saturated $NaHCO_3$ solution and saturated NaCl solution and dried with sodium sulfate. After the solvent is removed in a rotary evaporator, the crude product is chromatographed on silica gel (eluant: hexane/ethyl acetate 3:1 to 1:1). Then, it is purified again by means of HPLC. 650 mg (26%) of the desired product is obtained as a yellow solid.

Melting point: 110° C.

Moreover, the double-bond-isomeric compound (rac.) 2-{4-chloro-alpha-[(8-fluoro-2-methylquinazolin-5-yl)amino]-2-methoxybenzyl}-1,1,1-trifluoro-4-methylpent-3-en-2-ol can be isolated as a slightly polar by-product.

Melting point: 118° C.

The main product is separated into its enantiomers: 1. Chiralpak AD 20µ, Hex/EtOH 95/5, 2. Luna C18, $CH_3CN/H_2O$ 50/50.

MS (ESI): 484/486 (M+1), 516/518 (M+1+MeOH);
$^1$H-NMR (300 MHz, $CDCl_3$): δ=1.74 (s, 3H), 2.31 (d, J=14 Hz, 1H), 2.48 (d, J=14 Hz, 1H), 2.90 (s, 3H), 3.33 (s, 1H), 3.99 (s, 3H), 4.58 (s, 1H), 5.02 (s, 1H), 5.27 (d, J=7 Hz, 1H), 5.94 (s, J=7 Hz, 1H), 6.14 (dd, J=3/8 Hz, 1H), 6.90-6.95 (m, 2H), 7.22-7.28 (m, 1H), 7.36 (d, J=8 Hz, 1H), 9.42 (s, 1H).

(−)-Enantiomer: Melting point: 72-73° C.; HPLC: $R_t$=8.4 min (Chiralpak 10µ, 250×4.6 mm, Hex/EtOH 5%)

(+)-Enantiomer: Melting point: 70-71° C.; HPLC: $R_t$=11.9 min (Chiralpak 10µ, 250×4.6 mm, Hex/EtOH 5%)

EXAMPLE 8

2-{4-Bromo-alpha-[(1H-indazol-4-yl)amino]-2-methoxybenzyl}-1,1,1-trifluoro-4-methylpent-4-en-2-ol $^1$H-NMR (300 MHz, $CD_3OD$): δ=1.79 (3H), 2.28 (1H), 2.52 (1H), 4.00 (3H), 4.68 (1H), 4.81 (1H), 5.39 (1H), 5.98 (1H), 6.74 (1H), 7.00-7.12 (2H), 7.19 (1H), 7.45 (1H), 8.12 (1H) and 2-{4-Bromo-alpha-[(1H-indazol-4-yl)amino]-2-methoxybenzyl}-1,1,1-trifluoro-4-methylpent-3-en-2-ol (SL 4753-3)

$^1$H-NMR (300 MHz, $CD_3OD$): δ=1.39 (3H), 1.61 (3H), 3.98 (3H), 5.25 (1H), 5.39 (1H), 5.91 (1H), 6.75 (1H), 6.69-7.10 (2H), 7.10 (1H), 7.42 (1H), 8.13 (1H)

EXAMPLE 9

5-{[1-(4-Chloro-2-hydroxyphenyl)-2-hydroxy-4-methyl-2-(trifluoromethyl)-pent-3-en-1-yl]amino}-isocoumarin 5-{([4-(4-Chloro-2-methoxyphenyl)-2-hydroxy-4-methyl-2-(trifluoromethyl)pentylidene]amino}-isocoumarin 200 mg (0.616 mmol) of 4-(4-chloro-2-methoxyphenyl)-2-hydroxy-4-methyl-2-(trifluoromethyl)-pentanal is mixed with 99.3 mg (0.616 mmol) of 5-aminoisocoumarin (produced by reduction of the 5-nitroisocoumarin, described in Example 3, with zinc and ammonium chloride in EtOH, tetrahydrofuran, water) in 0.9 ml of glacial acetic acid, and it is stirred for four days at room temperature. The reaction mixture is drawn off three times with toluene, and the remaining residue is chromatographed on silica gel (mobile solvent ethyl acetate/hexane). 279.4 mg (96.9%) of the desired imine is isolated.

$^1$H-NMR (300 MHz, $CDCl_3$): δ=1.37 (3H), 1.58 (3H), 2.23 (1H), 2.42 (1H), 3.87 (3H), 4.64 (1H), 6.50 (1H), 6.10-6.19 (2H), 6.22 (1H), 7.03 (1H), 7.33 (1H), 7.35-7.46 (2H), 8.20 (1H)

5-{[1-(4-Chloro-2-hydroxyphenyl)-2-hydroxy-4-methyl-2-(trifluoromethyl)-pent-3-en-1-yl]amino}-isocoumarin 270 mg (0.577 mmol) of the above-described imine is mixed with 5.7 ml of a 1 M solution of BBr$_3$ in dichloromethane and stirred for two and a half hours at room temperature. After the usual working-up, the residue is chromatographed on a Flashmaster (NH$_2$ column, mobile solvent methanol/dichloromethane). 38.6 mg of the desired compound is isolated.

Melting point: 103-107° C.

EXAMPLE 10

2-{4-Fluoro-alpha-[(2-methylquinazolin-5-yl)amino]-2-methoxybenzyl}-1,1,1-trifluoro-4-methyl-pent-4-en-2-ol and 2-{4-fluoro-alpha-[(2-methylquinazolin-5-yl)amino]-2-methoxybenzyl}-1,1,1-trifluoro-4-methylpent-3-en-2-ol Analogously to Example 6, 340 mg (1.1 mmol) of 4-(4-fluoro-2-methoxyphenyl)-2-hydroxy-4-methyl-2-(trifluoromethyl)pentanal and 211 mg (1.32 mmol) of 5-amino-2-methylquinazoline (described in Example 6) are reacted with 0.46 ml (2.2 mmol) of titanium tetraethylate to form imine. After analogous rearrangement with boron tribromide and subsequent chromatography on silica gel with hexane-ethyl acetate (0-50%), 156 mg of a mixture that consists of 2-{4-fluoro-alpha-[(2-methylquinazolin-5-yl)amino]-2-methoxy-benzyl}-1,1,1-trifluoro-4-methylpent-4-en-2-ol and 2-{4-fluoro-alpha-[(2-methylquinazolin-5-yl)amino]-2-methoxybenzyl}-1,1,1-trifluoro-4-methylpent-3-en-2-ol is obtained. The separation is carried out by means of preparative thin-layer chromatography on silica gel (dichloromethane/2-propanol 5%) and yields 51 mg of the main component and 9 mg of the minor component.

$^1$H-NMR (300 MHz, CDCl$_3$) of the main component: δ=1.74 (s, 3H), 2.33 (d, 1H), 2.50 (d, 1H), 2.85 (s, 3H), 3.41 (s, 1H), 3.98 (s, 3H), 4.58 (s, 1H), 5.02 (s, 1H), 5.31 (d, 1H), 6.12 (d, 1H), 6.27 (d, 1H), 6.60-6.71 (m, 2H), 7.17 (d, 1H), 7.40 (dd, 1H), 7.50 (t, 1H), 9.39 (s, 1H).

$^1$H-NMR (300 MHz, CDCl$_3$) of the minor component: δ=1.45 (s, 3H), 1.64 (s,3H), 2.75 (s, 3H), 3.92 (s, 3H), 5.31 (s, 1H), 5.33 (d, 1H), 6.23 (d, 1H), 6.42 (d, 1H), 6.54-6.64 (m, 2H), 7.15 (d, 1H), 7.46 (dd, 1H), 7.53 (t, 1H), 9.46 (s, 1H).

EXAMPLE 11

2-{4-Fluoro-alpha-[(2-methylquinazolin-5-yl)amino]-2-methoxybenzyl}-1,1,1-trifluoro-4-methyl-pentan-2-ol 17 mg (0.04 mmol) of (rac.) 2-{4-fluoro-alpha-[(2-methylquinazolin-5-yl)amino]-2-methoxybenzyl}-1,1,1-trifluoro-4-methylpent-4-en-2-ol is shaken in 2 ml of methanol, 2 ml of ethyl acetate and 0.05 ml of triethylamine with 20 mg of palladium on carbon (10%) for 5 hours under hydrogen atmosphere. The reaction mixture is mixed with 200 mg of activated manganese dioxide and filtered through Celite after 10 minutes. It is concentrated by evaporation, and 3 mg of the desired product is obtained after preparative thin-layer chromatography on silica gel (cyclohexane/ethyl acetate 50%).

$^1$H-NMR (300 MHz CDCl$_3$); δ=0.83 (d, 3H), 0.91 (s, 3H), 1.78 (m, 1H), 2.85 (s, 3H), 3.98 (s, 3H), 5.25 (d, 1H), 6.10 (d, 1H), 6.35 (d, 1H), 6.63-6.72 (m, 2H), 7.19 (d, 1H), 7.40 (dd, 1H), 7.53 (t, 1H), 9.40 (s, 1H).

EXAMPLE 12

2-{4-Chloro-5-fluoro-alpha-[(2-methylquinazolin-5-yl)amino]-2-methoxybenzyl}-1,1,1-trifluoro-4-methylpent-4-en-2-ol Analogously to Example 6, 200 mg (0.58 mmol) of 4-(4-chloro-5-fluoro-2-methoxyphenyl)-2-hydroxy-4-methyl-2-(trifluoromethyl)pentanal and 111 mg (0.70 mmol) of 5-amino-2-methylquinazoline are reacted with 0.24 ml (1.16 mmol) of titanium tetraethylate to form imine. After analogous rearrangement with boron tribromide and subsequent chromatography on silica gel (dichloromethane/methanol 5%), 34 mg of the title compound is obtained.

$^1$H-NMR (300 MHz, CDCl$_3$); δ=1.45 (s, 3H), 1.64 (s, 3H), 2.75 (s, 3H), 3.92 (s, 3H), 5.31 (s, 1H), 5.33 (d, 1H), 6.23 (d, 1H), 6.42 (d, 1H), 6.54-6.64 (m, 2H), 7.15 (d, 1H), 7.46 (dd, 1H), 7.53 (t, 1H), 9.46 (s, 1H).

EXAMPLE 13

2-{4-Fluoro-alpha-[(7-fluoro-2-methylquinazolin-5-yl)amino]-2-methoxybenzyl}-1,1,1-trifluoro-4-methylpent-3-en-2-ol 5-Amino-7-fluoro-2-methyquinazoline 17 g (70.5 mmol) of 3,6-difluoro-2-N-pivaloylaminobenzaldehyde (L. Florvall, I. Fagervall, L.-G- Larsson, S. B. Ross, Eur. J. Med. Chem. 34 (1999) 137-151), 9.2 g of acetamidine hydrochloride, 13.4 g of potassium carbonate and 10.4 g of molecular sieve (4A) are added together in 70 ml of butyronitrile. It is heated to 145° C. while being stirred vigorously for 17 hours, and the solvent is removed in a vacuum. After the residue is chromatographed on silica gel with hexane/ethyl acetate (0-70%), 4.5 g of 7-fluoro-5-N-pivaloylamino-2-methyquinazoline is obtained.

1 g (3.82 mmol) of 7-fluoro-5-N-pivaloylamino-2-methyquinazoline is dissolved in 74 ml of toluene and cooled to −70° C. Over 30 minutes, 9.5 ml (11.4 mmol) of a 1.2 M diisobutyl aluminum hydride solution in toluene is added in drops. The reaction mixture is allowed to heat to −40° C., and it is stirred for 4 hours at −40° C. Water is slowly added, and it is stirred for 30 minutes until a precipitate forms, which is removed by means of filtration through Celite. The phases are separated, washed with saturated sodium chloride solution and dried on sodium sulfate. After chromatography on silica gel with hexane-ethyl acetate (0-100%), 64 mg of the product is obtained.

$^1$H-NMR (300 MHz, CDCl$_3$); δ=2.83 (s, 3H), 4.67 (br., 2H), 6.50 (dd, 1H), 6.93 (dd, 1H), 9.23 (s, 1H).

0.25 ml of titanium tetraethylate is added to 150 mg (0.48 mmol) of 4-(4-fluoro-2-methoxyphenyl)-2-hydroxy-4-methyl-2-(trifluoromethyl)-pentanal and 85 mg (0.48 mmol) of 5-amino-7-fluoro-2-methylquinazoline in 8 ml of toluene, and the mixture is heated to 100° C. over 2 hours. After cooling, it is poured into water, and vigorous stirring is continued. The suspension is filtered through Celite, and it is rewashed thoroughly with ethyl acetate. The phases of the filtrate are separated, and it is extracted again with ethyl acetate. It is dried on sodium sulfate, and the solvent is removed in a vacuum. 220 mg of 4-(4-fluoro-2-methoxyphenyl)-1-(7-fluoro-2-methylquinazolin-5-ylimino)-4-methyl-2-(trifluoromethyl)-pentan-2-ol that is thus obtained in crude form is taken up in 8 ml of dichloromethane, and it is cooled to −70° C. 3 ml (3 mmol) of a 1 M titanium tetrachloride solution in dichloromethane is added in drops over 10 minutes, and it is allowed to heat for 4 hours to room temperature. The solution is poured into a saturated sodium bicarbonate solution and vigorously stirred for 5 minutes. It is extracted with ethyl acetate, washed with saturated sodium chloride solution and dried on sodium sulfate. After concentration by evaporation and chromatography on silica gel (dichloromethane/methanol 10%), 25 mg of the desired product is obtained.

$^1$H-NMR (300 MHz, CDCl$_3$); δ=1.53 (s, 3H), 1.66 (s, 3H), 2.12 (d, 1H), 2.27 (d, 1H), 2.84 (s, 3H), 4.94 (d, 1H), 5.99 (s, 1H), 6.00 (s, 1H), 6.02 (d, 1H), 6.50 (dd, 1H), 6.68 (d, 1H), 6.83 (d, 1H), 6.89 (dd, 1H), 9.26 (s, 1H).

EXAMPLE 14

2-{6-Fluoro-alpha-[(8-fluoro-2-methylquinazolin-5-yl)amino]-2-hydroxybenzyl}-1,1,1-trifluoro-4-methylpent-4-en-2-ol Analogously to Example 6, 200 mg (0.65 mmol) of 4-(6-fluoro-2-methoxyphenyl)-2-hydroxy-4-methyl-2-(trifluoromethyl)pentanal and 141 mg (0.80 mmol) of 5-amino-8-fluoro-2-methylquinazoline (production described in Example 7) are reacted with 0.33 ml (1.58 mmol) of titanium tetraethylate to form imine. After analogous rearrangement with boron tribromide and subsequent chromatography on silica gel (hexane/acetone 50%), 28 mg of the title compound is obtained.

$^1$H-NMR (300 MHz, CDCl$_3$); δ=1.80 (s, 3H), 2.38 (d, 1H), 2.55 (d, 1H), 2.85 (s, 3H), 4.66 (s, 1H), 4.95 (s, 1H), 5.45 (d, 1H), 6.34 (d, 1H), 6.60-6.74 (m, 3H), 7.13 (m, 1H), 7.46 (t, 1H), 9.43 (s, 1H).

EXAMPLE 15

2-{4-Fluoro-alpha-[(2-methylphthalazin-1-on-5-yl)amino]-2-hydroxybenzyl}-1,1,1-trifluoro-4-methylpent-4-en-2-ol and 2-{4-Fluoro-alpha-[(2-methylphthalazin-1-on-5-yl)amino]-2-hydroxybenzyl}-1,1,1-trifluoro-4-methylpent-3-en-2-ol 3-Bromo-4-nitro-phthalide 5.37 g of 4-nitrophthalide (Tetrahedron Lett. (2001), 42, pp. 1647-50), 8.04 g of N-bromosuccinimide and 196 mg of benzoyl peroxide are heated in 80 ml of benzotrifluoride under reflux and with exposure to light until the reaction is completed. It is added to water, extracted with dichloromethane, washed several times with water, dried, and the solvent is removed in a vacuum. 7.24 g of 3-bromo-4-nitro-phthalide is obtained as a solid.

$^1$H-NMR (CDCl$_3$), δ (ppm)=7.26 (s, 1H), 7.88 (t, 1H), 8.3 (d, 1H), 8.56 (d, 1H)

5-Nitro-phthalazin-1-one 18.25 g of hydrazine sulfate and 14.88 g of sodium carbonate are stirred in 300 ml of DMF at 100° C. for 1 hour. Then, 7.24 g of 3-bromo-4-nitro-phthalide in 100 ml of DMF is added, and it is stirred for another 4 hours at 100° C. It is added to water, extracted several times with ethyl acetate, and the organic phase is washed with water and brine. It is dried, and the solvent is removed in a vacuum. After recrystallization from ethyl acetate, 2.35 g of 5-nitro-phthalazin-1-one is obtained as a solid.

$^1$H-NMR (DMSO), δ (ppm)=8.05 (t, 1H), 8.57-8.66 (m, 2H), 8.73 (s, 1H), 13.13 (bs, 1H)

2-Methy-5-nitro-phthalazin-1-one 1.6 g of 5-nitro-phthalazin-1-one and 2.31 g of potassium carbonate are stirred for 10 minutes at room temperature in 60 ml of DMF. 1.1 ml of methyl iodide is added, and it is stirred overnight. It is added to water, extracted several times with ethyl acetate, and the organic phase is washed with water and brine. It is dried, and the solvent is removed in a vacuum. 1.57 g of 2-methy-5-nitro-phthalazin-1-one is obtained as a yellow solid.

$^1$H-NMR (DMSO), δ (ppm)=3.73 (s, 3H), 8.05 (t, 1H), 8.62 (d, 2H), 8.75 (s, 1H)

5-Amino-2-methylphthalazin-1-one 1.57 g of 2-methy-5-nitrophthalazin-1-one and 130 mg of palladium on activated carbon are suspended in 45 ml of ethyl acetate and hydrogenated with hydrogen under normal pressure. It is filtered through diatomaceous earth, and the solvent is removed in a vacuum. 1.26 g of 5-amino-2-methylphthalazin-1-one is obtained as a yellow solid.

$^1$H-NMR (CDCl$_3$), δ (ppm)=3.81 (s, 3H), 7.0 (d, 1H), 7.5 (t, 1H), 7.8 (d, 1H), 8.16 (s, 1H)

2-{4-Fluoro-alpha-[(2-methylphthalazin-1-on-5-yl)amino]-2-hydroxybenzyl}-1,1,1-trifluoro-4-methylpent-4-en-2-ol and 2-{4-Fluoro-alpha-[(2-methylphthalazin-1-on-5-yl)amino]-2-hydroxybenzyl}-1,1,1-trifluoro-4-methylpent-3-en-2-ol Analogously to Example 6, 1.0 g of 4-(4-fluoro-2-methoxyphenyl)-2-hydroxy-4-methyl-2-(trifluoromethyl)pentanal and 560 mg of 5-amino-2-methylphthalazin-1-one are reacted with 3.8 ml of titanium tetraethylate to form imine. After analogous rearrangement with boron tribromide and subsequent HPLC chromatography, 110 mg of 2-{4-fluoro-alpha-[(2-methylphthalazin-1-on-5-yl)amino]-2-hydroxybenzyl}-1,1,1-trifluoro-4-methylpent-4-en-2-ol as a main compound and 38 mg of 2-{4-fluoro-alpha-[(2-methylphthalazin-1-on-5-yl)amino]-2-hydroxybenzyl}-1,1,1-trifluoro-4-methylpent-3-en-2-ol as a secondary compound are obtained.

Main compound: $^1$H-NMR (300 MHz, CD$_3$OD): δ=1.79 (s, 3H), 2.32 (d, 1H), 2.56 (d, 1H), 3.81 (s, 3H), 4.65 (s, 1H), 4.81 (s, 1H), 5.25 (s, 1H), 6.50 (dd, 1H), 6.57 (d, 1H), 6.90 (d, 1H), 7.36-7.55 (m, 3H), 8.52 (s, 1H)

Secondary compound: $^1$H-NMR (300 MHz, CD$_3$OD): δ=1.47 (s, 3H), 1.63 (s, 3H), 3.81 (s, 3H), 5.29 (s, 1H), 5.31 (s, 1H), 6.48 (dd, 1H), 6.54 (dd, 1H), 6.81 (d, 1H), 7.40-7.55 (m, 3H), 8.54 (s, 1H).

EXAMPLES 16 and 17

(−)-2-{4-Fluoro-alpha-[(2-methylphthalazin-1-on-5-yl)amino]-2-hydroxybenzyl}-1,1,1-trifluoro-4-methylpent-3-en-2-ol and (+)-2-{4-Fluoro-alpha-[(2-methylphthalazin-1-on-5-yl)amino]-2-hydroxybenzyl}-1,1,1-trifluoro-4-methylpent-3-en-2-ol Separation of (+/−)-2-{4-Fluoro-alpha-[(2-methylphthalazin-1-on-5-yl)amino]-2-hydroxybenzyl}-1,1,1-trifluoro-4-methylpent-3-en-2-ol The enantiomer mixture is separated by chromatography on chiral carrier material (CHIRALPAK AD®, DAICEL Company) with hexane/ethanol (93:7, vvv). Thus obtained are the (−)-enantiomer: MS (EI): M$^+$=451, [α]$_D$−169.8° (c=1.0, CHCl$_3$) and the (+)-enantiomer: MS (EI): M$^+$=451, [α]$_D$−146.3° (c=1.0, CHCl$_3$)

EXAMPLE 18
2-{4-Bromo-alpha-[(quinolin-2-on-5-yl)amino]-2-hydroxybenzyl}-1,1,1-trifluoro-4-methylpent-4-en-2-ol and 2-{4-Bromo-alpha-[(quinolin-2-on-5-yl)amino]-2-hydroxybenzyl}-1,1,1-trifluoro-4-methylpent-3-en-2-ol 5-Aminoquinolin-2(1H)-one 4.5 g of 5-nitroquinolin-2(1H)-one (Chem. Pharm. Bull. (1981), 29, pp. 651-56) is hydrogenated in 200 ml of ethyl acetate and 500 ml of methanol in the presence of 45 mg of palladium on activated carbon as a catalyst under normal pressure with hydrogen until the reaction is completed. The catalyst is removed by filtration through diatomaceous earth, and the reaction solution is concentrated by evaporation in a vacuum. 3.8 g of the title compound is obtained as a yellow solid.

$^1$H-NMR (DMSO): δ=5.85 (bs, 2H), 6.27 (d, 1H), 6.33 (d, 1H), 6.43 (d, 1H), 7.10 (t, 1H), 8.07 (d, 1H), 11.39 (bs, 1H)

Analogously to Example 6, 800 mg of 4-(4-bromo-2-methoxyphenyl)-2-hydroxy-4-methyl-2-(trifluoromethyl)pentanal and 348 mg of 5-amino-quinolin-2-one are reacted with 2.5 ml of titanium tetraethylate to form imine. After analogous rearrangement with boron tribromide and subsequent chromatography on silica gel, 53 mg of 2-{4-bromo-alpha-[(quinolin-2-on-5-yl)amino]-2-hydroxybenzyl}-1,1,1-trifluoro-4-methylpent-4-en-2-ol (fraction A) and 54 mg of 2-{4-bromo-alpha-[(quinolin-2-on-5-yl)amino]-2-hydroxybenzyl}-1,1,1-trifluoro-4-methylpent-3-en-2-ol (fraction B) are obtained.

Fraction A: $^1$H-NMR (300 MHz, CD$_3$OD): δ=1.78 (s, 3H), 2.31 (d, 1H), 2.59 (d, 1H), 4.67 (s, 1H), 4.82 (s, 1H), 5.26 (s, 1H), 6.29 (d, 1H), 6.55 (d, 1H), 6.62 (d, 1H), 6.96 (dd, 1H), 7.01 (d, 1H), 7.22 (t, 1H), 7.33 (d, 1H), 8.21 (d, 1H).

Fraction B: $^1$H-NMR (300 MHz, CD$_3$OD): δ=1.46 (s, 3H), 1.62 (s, 3H), 5.28 (s, 1H), 5.32 (d, 1H), 6.23 (d, 1H), 6.55 (d, 1H), 6.60 (d, 1H), 6.89 (dd, 1H), 6.94 (d, 1H), 7.21 (t, 1H), 7.32 (d, 1H), 8.22 (d, 1H).

EXAMPLE 19
4-Chloro-5-fluoro-β-[(7-fluoro-2-methylquinazolin-5-yl)amino]-2-methoxy-α-(2-methyl-2-propenyl)-α-(trifluoromethyl)benzene Ethanol Analogously to Example 6, 200 mg (0.58 mmol) of 4-(4-chloro-5-fluoro-2-methoxyphenyl)-2-hydroxy-4-methyl-2-(trifluoromethyl)pentanal and 123 mg (0.70 mmol) of 5-amino-7-fluoro-2-methylquinazoline are reacted with 0.24 ml (1.16 mmol) of titanium tetraethylate to form imine. After analogous rearrangement with boron tribromide and subsequent chromatography on silica gel (hexane/ethyl acetate 33%), 51 mg of the title compound is obtained.

$^1$H-NMR (CDCl$_3$); δ=1.78 (s, 3H), 2.26 (d, 1H), 2.52 (d, 1H), 2.77 (s, 3H), 4.05 (s, 3H), 4.66 (s, 1H), 4.82 (s, 1H), 5.33 (s, 1H), 6.22 (dd, 1H), 6.73 (dd, 1H), 7.22 (d, 1H), 7.62 (d, 1H), 9.55 (s, 1H).

EXAMPLES 20 and 21
(−)-4-Chloro-5-fluoro-β-[(2-methylquinazolin-5-yl)amino]-α-(2-methyl-2-propenyl)-2-methoxy-α-(trifluoromethyl)benzene Ethanol and (+)-4-Chloro-5-fluoro-β-[(2-methylquinazolin-5-yl)amino]-α-(2-methyl-2-propenyl)-2-methoxy-α-(trifluoromethyl)benzene Ethanol (rac)-4-Chloro-5-fluoro-β-[(2-methylquinazolin-5-yl)amino]-α-(2-methyl-2-propenyl)-2-methoxy-α-(trifluoromethyl)benzene ethanol is cleaved by means of preparative chiral HPLC (Chiralpak AD 20 µM) into the enantiomer-pure compounds:

(−)-enantiomer: analytic HPLC: R$_t$=8.4 min (Chiralpak AD-H 5µ, 150×4.6 mm, hexane/iso-propanol 5%, 1 ml/min of flow)

(+)-enantiomer: analytic HPLC: R$_t$=10.1 min (Chiralpak AD-5µ, 150×4.6 mm, hexane/iso-propanol 5%, 1 ml/min of flow)

EXAMPLE 22
3-Chloro-2-fluoro-β-[(7-fluoro-2-methylquinazolin-5-yl)amino]-2-hydroxy-α-(2-methyl-1-propenyl)-α-(trifluoromethyl)benzene Ethanol 312 mg (0.622 mmol) of the imine 4-(4-chloro-3-fluoro-2-methoxyphenyl)-1,1,1-trifluoro-2-{[7-fluoro-2-methylquinazolin-5-ylimino]-methyl}-4-methyl-pentan-2-ol, produced as usual, is mixed with 6.4 ml of boron tribromide (1 M in dichloromethane) and stirred for two hours at room temperature. After the usual working-up and chromatography on a Flashmaster, 1.6 mg (0.52%) of the desired compound is obtained.

$^1$H-NMR (CD$_3$OD): δ=1.33 (3H), 1.62 (3H), 2.79 (3H), 5.09 (1H), 4.92 (1H, lies under the water peak of the methanol), 6.43 (1H), 6.50-6.70 (2H), 76.95 (1H), 9.49 (1H).

EXAMPLES 23 and 24
(−)2-{4-Chloro-α-[(8-fluoro-2-methylquinazolin-5-yl)amino]-2-methoxybenzyl}-1,1,1-trifluoro-4-methylpent-3-en-2-ol and (+) 2-{4-Chloro-α-[(8-fluoro-2-methylquinazolin-5-yl)amino]-2-methoxybenzyl}-1,1,1-trifluoro-4-methylpent-3-en-2-ol The by-product (rac) 2-{4-chloro-α-[(8-fluoro-2-methylquinazolin-5-yl)amino]-2-methoxybenzyl}-1,1,1-trifluoro-4-methylpent-3-en-2-ol from Example 7 is separated into its enantiomers with the aid of the chiral preparative HPLC. Column: Chiralpak AD 10µ (250×20 mm); eluant hexane/7% isocratic 2-propanol; flow: 20 ml/min. Analysis: Chiralpak AD 10µ (205×4.6 mm); eluant hexane/7% isocratic 2-propanol; flow: 1.0 ml/min; 25° C.

The (−)-enantiomer comes at a retention time of R$_t$=10.35 min; spec. optical rotation: −278.3 (c=0.230; CHCl$_3$). The (+)-enantiomer comes at a retention time of R$_t$=15.41 min.

EXAMPLES 25 and 26
(−)-2-{4-Fluoro-alpha-[(2-methylphthalazin-1-on-5-yl)amino]-2-hydroxybenzyl}-1,1,1-trifluoro-4-methylpent-4-en-2-ol and (+)-2-{4-Fluoro-alpha-[(2-methylphthalazin-1-on-5-yl)amino]-2-hydroxybenzyl}-1,1,1-trifluoro-4-methylpent-4-en-2-ol Separation of (+/−)-2-{4-Fluoro-alpha-[(2-methylphthalazin-1-on-5-yl)amino]-2-hydroxybenzyl}-1,1,1-trifluoro-4-methylpent-4-en-2-ol The enantiomer mixture is separated by chromatography on chiral carrier material (CHIRALPAK AD®, DAICEL Company) with hexane/ethanol (93:7, vvv). Thus obtained are the (−)-enantiomer: MS (EI): M$^+$=451, [α]$_D$−224.3° (c=1.0, CHCl$_3$) and the (+)-enantiomer: MS (EI): M$^+$=451, [α]$_D$+207.6 (c=1.0, CHCl$_3$)

EXAMPLE 27

2-{4-Chloro-alpha-[(phthalazin-1-on-5-yl)amino]-2-methoxybenzyl}-1,1,1-trifluoro-4-methylpent-4-en-2-ol and 2-{4-Chloro-alpha-[(phthalazin-1-on-5-yl)amino]-2-methoxybenzyl}-1,1,1-trifluoro-4-methylpent-3-en-2-ol 5-Amino-phthalazin-1-one 980 mg of 5-nitro-phthalazin-1-one (Example 66) and 100 mg of palladium on activated carbon are suspended in 50 ml of ethyl acetate and 1 ml of triethylamine and hydrogenated with hydrogen under normal pressure. It is filtered through diatomaceous earth, and the solvent is removed in a vacuum. As a crude product, 830 mg of 5-amino-phthalazin-1-one is obtained as a solid.

$^1$H-NMR (DMSO), δ (ppm)=6.26 (bs, 2H), 7.00 (d, 1H), 7.32 (d, 1H), 7.44 (t, 1H), 8.48 (s, 1H), 12.35 (bs, 1H)

Analogously to Example 6, 500 mg of 4-(4-chloro-2-methoxyphenyl)-2-hydroxy-4-methyl-2-(trifluoromethyl)pentanal and 250 mg of 5-amino-phthalazin-1-one are reacted with 1.8 ml of titanium tetraethylate to form imine. After analogous rearrangement with boron tribromide and subsequent chromatography on silica gel, 38 mg of 2-{4-chloro-alpha-[(phthalazin-1-on-5-yl)amino]-2-methoxybenzyl}-1,1,1-trifluoro-4-methylpent-4-en-2-ol (fraction A) and 47 mg of 2-{4-chloro-alpha-[(phthalazin-1-on-5-yl)amino]-2-methoxybenzyl}-1,1,1-trifluoro-4-methylpent-3-en-2-ol (fraction B) are obtained.

Fraction A: $^1$H-NMR (300 MHz, CD$_3$OD): δ=1.80 (s, 3H), 2.27 (d, 1H), 2.52 (d, 1H), 4.04 (s, 3H), 4.67 (s, 1H), 4.84 (s, 1H), 5.35 (s, 1H), 6.80 (d, 1H), 6.97 (dd, 1H), 7.11 (d, 1H), 7.47-7.63 (m, 3H), 8.55 (s, 1H).

Fraction B: $^1$H-NMR (300 MHz, CD$_3$OD): δ=1.37 (s, 3H), 1.62 (s, 3H), 3.98 (s, 3H), 5.25 (s, 1H), 5.32 (s, 1H), 6.70 (d, 1H), 6.91 (dd, 1H), 7.04 (d, 1H), 7.44-7.62 (m, 3H), 8.57 (s, 1H).

EXAMPLE 28

5-{[4-Chloro-5-fluoro-2-methoxy-α-(2-methyl-1-propenyl)-α-(trifluoromethyl)benzene Ethanol-β-yl]amino}-2-methylphthalazin-1-one Analogously to Example 6, 260 mg (0.76 mmol) of 4-(4-chloro-5-fluoro-2-methoxyphenyl)-2-hydroxy-4-methyl-2-(trifluoromethyl)pentanal and 160 mg (0.91 mmol) of 5-amino-2-methyl-phthalazin-1-one are reacted with 0.3 ml (1.5 mmol) of titanium tetraethylate to form imine. After analogous rearrangement with boron tribromide and subsequent chromatography on silica gel (hexane/ethyl acetate 0-50%), 70 mg of the title compound is obtained.

$^1$H-NMR (CDCl$_3$); δ=1.64 (s, 3H), 1.67 (s, 3H), 3.84 (s, 3H), 3.92 (s, 3H), 5.20 (s, 1H), 5.24 (br, 1H), 5.69 (br, 1H), 6.46 (d, 1H), 6.89 (d, 1H), 7.22 (d, 1H), 7.35 (t, 1H), 7.63 (d, 1H), 8.19 (s, 1H).

The invention claimed is:

1. A compound of formula I

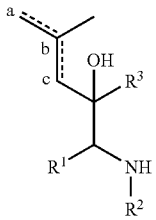

(I)

in which

R$^1$ means an optionally substituted phenyl radical,

R$^2$ means a monocyclic, or bicyclic, aromatic, partially aromatic, or non-aromatic ring system, which optionally contains 1-3 nitrogen atoms, 1-2 oxygen atoms and/or 1-2 sulfur atoms and optionally is substituted in one or more places by a radical that is selected from the group carbonyl, halogen, hydroxy, or (C$_1$-C$_5$)-alkyl, which optionally can be substituted by 1-3 hydroxy groups, 1-3 (C$_1$-C$_5$)alkoxy groups and/or 1-3 COOR$^6$ groups, (C$_1$-C$_5$)alkoxy, (C$_1$-C$_5$)-alkylthio, (C$_1$-C$_5$)-perfluoroalkyl, cyano, nitro, or two substituents together form a group that is selected from the groups —O—(CH$_2$)$_n$—O—, —O—(CH$_2$)$_n$—CH$_2$—, —O—CH═CH—, —(CH$_2$)$_{n+2}$—, —NH—(CH$_2$)$_{n+1}$—, —N(C$_1$-C$_3$-alkyl)-(CH$_2$)$_{n+1}$—, and —NH—N═CH—, whereby n=1 or 2, and the terminal oxygen atoms and/or carbon atoms and/or nitrogen atoms are linked to directly adjacent ring-carbon atoms,

NR$^4$R$^5$, whereby R$^4$ and R$^5$, independently of one another, can be hydrogen, C$_1$-C$_5$-alkyl or (CO)—C$_1$-C$_5$-alkyl,

COOR$^6$, whereby R$^6$ means hydrogen or a C$_1$-C$_5$-alkyl group, (CO)NR$^7$R$^8$, whereby R$^7$ and R$^8$, independently of one another, mean hydrogen or a C$_1$-C$_5$-alkyl group, or a (C$_1$-C$_5$-alkylene)—O—(CO)—(C$_1$-C$_5$)alkyl group, R$^3$ means a C$_1$-C$_3$-alkyl group or a partially or completely fluorinated C$_1$-C$_3$-alkyl group, and the broken line means a double bond between atoms a and b or a double bond between atoms b and c or only a single bond between atoms a and b, as well as b and c, racemates, separately present stereoisomers, or physiologically compatible salts thereof.

2. A compound of formula I

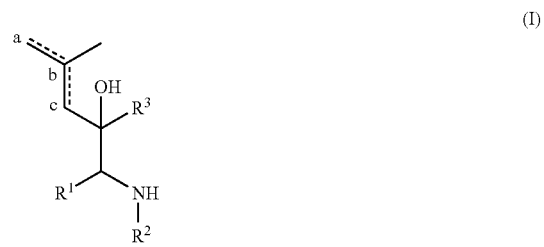

(I)

in which

R$^1$ means an optionally substituted phenyl radical,

R$^2$ means a monocyclic or bicyclic aromatic, partially aromatic or non-aromatic ring system, which optionally contains 1-3 nitrogen atoms, 1-2 oxygen atoms and/or 1-2 sulfur atoms and optionally is substituted in one or more places by a radical that is selected from the group carbonyl, halogen, hydroxy, (C$_1$-C$_5$)-alkyl, which optionally can be substituted by 1-3 hydroxy groups, 1-3 (C$_1$-C$_5$)alkoxy groups and/or 1-3 COOR$^6$ groups, ($C_1$-$C_5$)alkoxy, ($C_1$-$C_5$)-alkylthio, ($C_1$-$C_5$)-perfluoroalkyl, cyano, nitro, or $NR^4R^5$, whereby $R^4$ and $R^5$, independently of one another, can be hydrogen, $C_1$-$C_5$-alkyl or (CO)—$C_1$-$C_5$-alkyl, $COOR^6$, whereby $R^6$ means hydrogen or a $C_1$-$C_5$-alkyl group, (CO)$NR^7R^8$, whereby $R^7$ and $R^8$, independently of one another, mean hydrogen or a $C_1$-$C_5$-alkyl group, or a ($C_1$-$C_5$-alkylene)-O—(CO)—($C_1$-$C_5$)alkyl group, $R^3$ means a $C_1$-$C_3$-alkyl group or a partially or completely fluorinated $C_1$-$C_3$-alkyl group, and the dotted line means a double bond between atoms a and b or a double bond between atoms b and c or only a single bond between atoms a and b as well as b and c, racemates, separately present stereoisomers or physiologically compatible salts thereof.

3. Compounds according to claim 1, in which the phenyl radical is substituted by one or more radicals from the group $C_1$-$C_5$-alkyl, $C_1$-$C_5$-alkoxy, $C_1$-$C_5$-alkylthio, $C_1$-$C_5$-perfluoroalkyl, halogen, hydroxy, cyano, nitro, —O—$(CH_2)_n$—O—, —O—$(CH_2)_n$—$CH_2$—, —O—CH═CH—, —$(CH_2)_{n+2}$—, —NH—$(CH_2)_{n+1}$, $N(C_1$-$C_3$-alkyl)-$(CH_2)_{n+1}$, or —NH—N═CH—, whereby n=1 or 2, and the terminal oxygen atoms and/or carbon atoms are linked with directly adjacent ring-carbon atoms, or $NR^4R^5$, whereby $R^4$ and $R^5$, independently of one another, can be hydrogen, $C_1$-$C_5$-alkyl or (CO)—$C_1$-$C_5$-alkyl.

4. Compounds according to claim 1, in which $R^2$ means an optionally substituted phthalidyl, isoindolyl, dihydroindolyl, dihydroisoindolyl, dihydroisoquinolinyl, thiophthalidyl, benzoxazinonyl, phthalazinonyl, quinolinyl, isoquinolinyl, quinolonyl, isoquinolonyl-, indazolyl, benzothiazolyl, quinazolinyl, quinoxalinyl, cinnolinyl, phthalazinyl, 1,7- or 1,8-naphthyridinyl, dihydroindolonyl, dihydroisoindolonyl, benzimidazole or indolyl group that is linked via any position.

5. Compounds according to claim 1, in which $R^3$ stands for a trifluoromethyl or pentafluoroethyl radical.

6. A method for the production of pharmaceutical agents, comprising combining a compound according to claim 1 and a pharmaceutically acceptable carrier.

7. Compounds according to claim 1, in which the phthalidyl, isoindolyl, dihydroindolyl, dihydroisoindolyl, dihydroisoquinolinyl, thiophthalidyl, benzoxazinonyl, phthalazinonyl, quinolinyl, isoquinolinyl, quinolonyl, isoquinolonyl, indazolyl, benzothiazolyl, quinazolinyl, quinoxalinyl, cinnolinyl, coumarinyl, isocoumarinyl, phthalazinyl, 1,7- or 1,8-naphthyridinyl, dihydroindolonyl, dihydroisoindolonyl, benzimidazole or indolyl group $R^2$ is substituted with 0 to 3 of the same or different radicals from the group $C_1$-$C_3$-alkyl, hydroxy, carbonyl or halogen.

8. A process for the production of compounds of formula I,

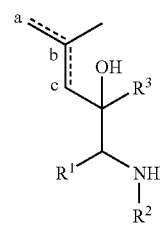

(I)

in which
$R^1$ means an optionally substituted phenyl radical,
$R^2$ means a monocyclic, or bicyclic, aromatic, partially aromatic, or non-aromatic ring system, which optionally contains 1-3 nitrogen atoms, 1-2 oxygen atoms and/or 1-2 sulfur atoms and optionally is substituted in one or more places by a radical that is selected from the group carbonyl, halogen, hydroxy, or ($C_1$-$C_5$)-alkyl, which optionally can be substituted by 1-3 hydroxy groups, 1-3 ($C_1$-$C_5$)alkoxy groups and/or 1-3 $COOR^6$ groups, ($C_1$-$C_5$)alkoxy, ($C_1$-$C_5$)-alkylthio, ($C_1$-$C_5$)-perfluoroalkyl, cyano, nitro, or two substituents together form a group that is selected from the groups —O—$(CH_2)_n$—O—, —O—$(CH_2)_n$—$CH_2$—, —O—CH═CH—, —$(CH_2)_{n+2}$—, —NH—$(CH_2)_{n+1}$—, —N($C_1$-$C_3$-alkyl)-$(CH_2)_{n+1}$—, and —NH—N═CH—, whereby n=1 or 2, and the terminal oxygen atoms and/or carbon atoms and/or nitrogen atoms are linked to directly adjacent ring-carbon atoms,
$NR^4R^5$,
whereby $R^4$ and $R^5$, independently of one another, can be hydrogen, $C_1$-$C_5$-alkyl or (CO)—$C_1$-$C_5$-alkyl, $COOR^6$,
whereby $R^6$ means hydrogen or a $C_1$-$C_5$-alkyl group, (CO)$NR^7R^8$,
whereby $R^7$ and $R^8$, independently of one another, mean hydrogen or a $C_1$-$C_5$-alkyl group,
or a ($C_1$-$C_5$-alkylene)-O—(CO)—($C_1$-$C_5$)alkyl group,
$R^3$ means a $C_1$-$C_3$-alkyl group or a partially or completely fluorinated $C_1$-$C_3$-alkyl group,
and the broken line means a double bond between atoms a and b or a double bond between atoms b and c or only a single bond between atoms a and b, as well as b and c, racemates, separately present stereoisomers, or physiologically compatible salts thereof, comprising reacting imines of formula II

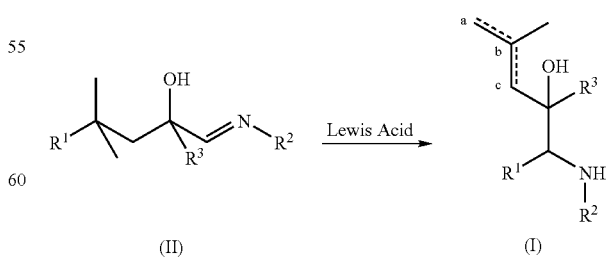

with Lewis acid in an organic solvent, to obtain compounds of formula I.

9. A method for the treatment of an inflammatory disease in a host in need thereof, comprising administering to said host an effective amount of a compound of formula I

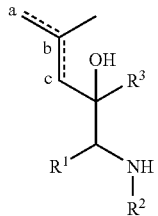

(I)

in which

R$^1$ means an optionally substituted phenyl radical,

R$^2$ means a monocyclic, or bicyclic, aromatic, partially aromatic, or non-aromatic ring system, which optionally contains 1-3 nitrogen atoms, 1-2 oxygen atoms and/or 1-2 sulfur atoms and optionally is substituted in one or more places by a radical that is selected from the group carbonyl, halogen, hydroxy, or (C$_1$-C$_5$)-alkyl, which optionally can be substituted by 1-3 hydroxy groups, 1-3 (C$_1$-C$_5$)alkoxy groups and/or 1-3 COOR$^6$ groups, (C$_1$-C$_5$)alkoxy, (C$_1$-C$_5$)-alkylthio, (C$_1$-C$_5$)-perfluoroalkyl, cyano, nitro, or two substituents together form a group that is selected from the groups —O—(CH$_2$)$_n$—O—, —O—(CH$_2$)$_n$—CH$_2$—, —O—CH=CH—, —(CH$_2$)$_{n+2}$—, —NH—(CH$_2$)$_{n+1}$—, —N(C$_1$-C$_3$-alkyl)-(CH$_2$)$_{n+1}$—, and —NH—N=CH—, whereby n=1 or 2, and the terminal oxygen atoms and/or carbon atoms and/or nitrogen atoms are linked to directly adjacent ring-carbon atoms,

NR$^4$R$^5$, whereby R$^4$ and R$^5$, independently of one another, can be hydrogen, C$_1$-C$_5$-alkyl or (CO)—C$_1$-C$_5$-alkyl, COOR$^6$, whereby R$^6$ means hydrogen or a C$_1$-C$_5$-alkyl group, (CO)NR$^7$R$^8$, whereby R$^7$ and R$^8$, independently of one another, mean hydrogen or a C$_1$-C$_5$-alkyl group, or a (C$_1$-C$_5$-alkylene)-O—(CO)—(C$_1$-C$_5$)alkyl group, R$^3$ means a C$_1$-C$_3$-alkyl group or a partially or completely fluorinated C$_1$-C$_3$-alkyl group, and the broken line means a double bond between atoms a and b or a double bond between atoms b and c or only a single bond between atoms a and b, as well as b and c, racemates, separately present stereoisomers, or physiologically compatible salts thereof.

10. A method according to claim 9, in which the phthalidyl, isoindolyl, dihydroindolyl, dihydroisoindolyl, dihydroisoquinolinyl, thiophthalidyl, benzoxazinonyl, phthalazinonyl, quinolinyl, isoquinolinyl, quinolonyl, isoquinolonyl, indazolyl, benzothiazolyl, quinazolinyl, quinoxalinyl, cinnolinyl, phthalazinyl, 1,7- or 1,8-naphthyridinyl, dihydroindolonyl, dihydroisoindolonyl, benzimidazole or indolyl group R$^2$ is substituted with methyl, chlorine or fluorine.

* * * * *